(12) United States Patent     (10) Patent No.: US 8,334,393 B2
Goldfinger et al.     (45) Date of Patent: Dec. 18, 2012

(54) CHIRAL COMPOUNDS AND LIQUID CRYSTAL COMPOSITIONS AND POLYMER NETWORKS DERIVED THEREFROM

(75) Inventors: Marc B. Goldfinger, West Chester, PA (US); Jose Manuel Rodriguez-Parada, Hockessin, DE (US); Lee A. Silverman, Newark, DE (US); Kai Qi, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/050,211

(22) Filed: Mar. 17, 2011

(65) Prior Publication Data

US 2011/0163267 A1     Jul. 7, 2011

Related U.S. Application Data

(62) Division of application No. 11/731,290, filed on Mar. 30, 2007, now Pat. No. 7,914,700.

(51) Int. Cl.
    *C07D 493/04*     (2006.01)
    *C07D 307/93*     (2006.01)
    *C07C 67/08*     (2006.01)
    *C07C 67/14*     (2006.01)

(52) U.S. Cl. ........... 549/464; 549/465; 549/473; 560/98

(58) Field of Classification Search .................. 549/464, 549/465, 473; 526/270; 560/98
See application file for complete search history.

(56) References Cited

U.S. PATENT DOCUMENTS

| 4,614,619 | A | 9/1986 | Shannon |
| 4,637,896 | A | 1/1987 | Shannon |
| 5,506,704 | A | 4/1996 | Broer et al. |

(Continued)

FOREIGN PATENT DOCUMENTS

DE     4408170 A1     9/1995

(Continued)

OTHER PUBLICATIONS

Pretsch et. al., Tables of Spectral Data for Structure Determination of Organic Compounds, 2nd Edition, 1989, pp. 141-142.
Peter A. Lander et. al., Asymetric Synthesis of X-Amino Acids by Copper-Catalyzed Conjugate Adddition of Grignard Reagents to Optically Active Carbamatacrylates, J. Am. Chem. Soc., 1994, vol. 116.8126-8132.
Aileen A. Craig et. al., Effect of Spacer Length on the Thermal Properties of Side-Chain Liquid Crystal Polymethacrylates, 2, Synthesis and Characterization of the Poly[w-{4'-cyanobiphenyl-4-yloxy) alkyl methacrylate}s, Macromolecules, 1995, vol. 28:3617-3624.
Alexey Bobrovsky, et al., A Study of Photooptical Processes in Photosensitive Cholesteric Azobenzene—Containing Polymer Mixture under an Action of the Polarized and Nonpolarized Light, Sciencedirect, Aug. 27, 2005.

(Continued)

Primary Examiner — Shean C Wu
(74) Attorney, Agent, or Firm — Kevin S. Dobson

(57) ABSTRACT

The invention relates to compounds of formula (I):

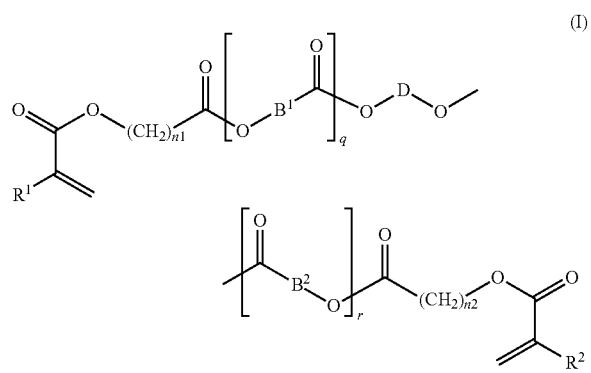

wherein $R^1$ and $R^2$ are each independently selected from the group: H, F, Cl and $CH_3$; $n1$ and $n2$ are each independently integers 3 to 20; q and r are each independently integers 0, 1 or 2, with the proviso that $q+r$ is $\geq 1$; D is a divalent chiral radical selected from the group:

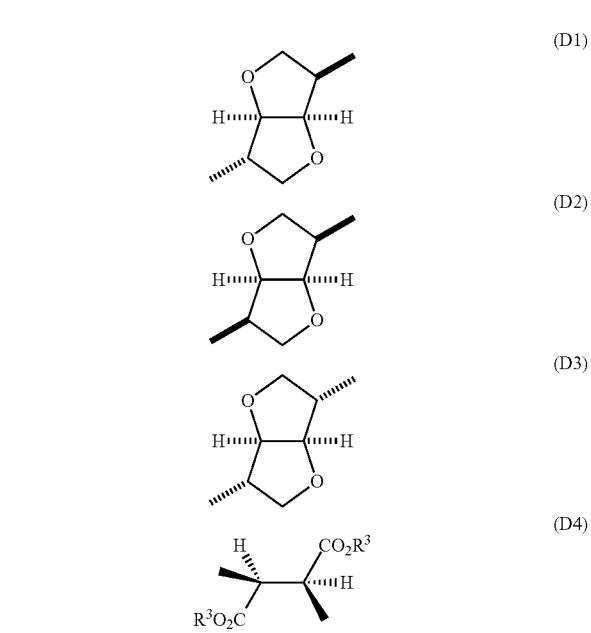

wherein $R^3$ is a C1 to C6 straight or branched chain alkyl group; and each $B^1$ and $B^2$ is a divalent radical independently selected from the group: $R^4$-substituted-1,4-phenyl, wherein $R^4$ is H, $—CH_3$ or $—OCH_3$; 2,6-naphthyl; and 4,4'-biphenyl; with the provisos that when $q+r=3$, at least one of $B^1$ and $B^2$ is $R^4$-substituted-1,4-phenyl; and when $q+r=4$, at least two of $B^1$ and $B^2$ are $R^4$-substituted-1,4-phenyl. The invention further relates to liquid crystal compositions comprising compounds of formula (I) and polymer networks derived from the polymerization of the liquid crystal compositions.

6 Claims, No Drawings

U.S. PATENT DOCUMENTS

| | | | |
|---|---|---|---|
| 5,560,864 A | 10/1996 | Goulding | |
| 5,780,629 A | 7/1998 | Etzbach et al. | |
| 5,793,456 A | 8/1998 | Broer et al. | |
| 5,833,880 A | 11/1998 | Siemensmeyer et al. | |
| 5,885,242 A | 3/1999 | Arick et al. | |
| 5,942,030 A * | 8/1999 | Schuhmacher et al. | 106/493 |
| 6,010,643 A | 1/2000 | Coates et al. | |
| 6,060,042 A * | 5/2000 | Schuhmacher et al. | 424/60 |
| 6,120,859 A | 9/2000 | Buchecker et al. | |
| 6,217,792 B1 * | 4/2001 | Parri et al. | 252/299.61 |
| 6,410,130 B1 | 6/2002 | Schuhmacher et al. | |
| 6,468,444 B1 | 10/2002 | Meyer | |
| 6,607,677 B1 | 8/2003 | Buchecker et al. | |
| 6,723,395 B2 | 4/2004 | May et al. | |
| 6,887,455 B2 | 5/2005 | Carpenter et al. | |
| 7,119,161 B2 | 10/2006 | Lawandy | |
| 7,736,532 B2 * | 6/2010 | Silverman et al. | 252/299.01 |
| 7,744,970 B2 * | 6/2010 | Silverman et al. | 428/1.3 |
| 7,749,577 B2 * | 7/2010 | Goldfinger et al. | 428/1.3 |
| 7,914,700 B2 * | 3/2011 | Goldfinger et al. | 252/299.01 |
| 2005/0224754 A1 | 10/2005 | Hirai | |
| 2007/0116945 A1 * | 5/2007 | Goldfinger et al. | 428/323 |
| 2007/0152188 A1 * | 7/2007 | Silverman et al. | 252/299.01 |
| 2007/0154718 A1 * | 7/2007 | Silverman et al. | 428/411.1 |
| 2007/0228326 A1 | 10/2007 | Goldfinger | |
| 2007/0267599 A1 | 11/2007 | Goldfinger | |
| 2009/0161061 A1 | 6/2009 | Qi | |
| 2010/0079721 A1 * | 4/2010 | Qi et al. | 349/195 |
| 2010/0308265 A1 * | 12/2010 | Goldfinger | 252/299.61 |
| 2010/0308270 A1 * | 12/2010 | Goldfinger | 252/299.64 |

FOREIGN PATENT DOCUMENTS

| | | |
|---|---|---|
| EP | 0261712 A1 | 3/1988 |
| EP | 331233 A2 | 6/1989 |
| EP | 0331233 B1 | 9/1989 |
| EP | 0397263 A1 | 11/1990 |
| EP | 0397263 B1 | 12/1994 |
| EP | 1038941 | 2/2000 |
| EP | 734852 B | 12/2002 |
| JP | 04-281403 | 7/1992 |
| JP | 1994/016616 | 1/1994 |
| JP | 2000-122059 | 4/2000 |
| JP | 2005-004389 | 1/2005 |
| WO | 95/16007 | 6/1995 |
| WO | 98/47979 A1 | 10/1998 |
| WO | 99/58334 | 11/1999 |
| WO | 01/60604 | 8/2001 |
| WO | 02/066493 A2 | 8/2002 |
| WO | 2006/128090 | 11/2006 |
| WO | 2006/128091 | 11/2006 |
| WO | 2009/23759 | 2/2009 |
| WO | 2009/23762 | 2/2009 |

OTHER PUBLICATIONS

P.G. De Gennes et. al., The Physcis of Liquid Crystals, 1995, Oxford University Press (Book not Included).

H. Bassler, et al., Helical Twisting Power of Steroidal Solutes in Cholesteric Mesophases, J. Chem Phys., 1970, vol. 52:631-637.

Dirk J. Broer et. al., Oriented Polymer Networks from a Mesogenic Diacrylate, Makromol. Chem., 1989, vol. 190:2255-2268.

Seiji Kurihara et. al., Preparation of Helical Polyelectrolyte Networks by Polymerizationo f Hydrogen Bonding Liquid Crystalline Monomers, Macromolecules, 1988, vol. 3:5940-5942.

Dirk J. Broer et. al., In-Situ Photopolymerization of Oriented Liquid-Crystalline Acrylates, 5), Makromol. Chem., 1991, vol. 192:59-74.

Chain-Shu et. al., Preparation of Liquid-Crystal Thermosets: In Situ Photopolymerization of Oriented Liquid—Crystal Diacrylates, J. Polym. Sci., Part A: Polym. Chem, 1999, vol. 37:3929-3935.

Dirk J. Broer et. al., In-Situ Photopolymerization of Oriented Liquid-Crystalline Acrylates, 4, Influence of a Lateral Mthyl Substituent on Monomer and Oriented Polymer Network Properties of a Mesogenic Diacrylate, Makromol. Chem., 1989, vol. 190:3201-3215.

Shibaev. et. al., Thermotropic Liquid Crysalline Polymers, Optical and Structural Properties of New Nematic and Cholesteric Polymets, Polymer Bulletin, 1982, vol. 6:485-492.

E.V. Dehmlow, Phase-Transfer Catalyzed Two-Phase Reactions in Preparative Organic Chemistry, Angewante Chemie, International Edition, 1974, vol. 13:170-179.

* cited by examiner

CHIRAL COMPOUNDS AND LIQUID CRYSTAL COMPOSITIONS AND POLYMER NETWORKS DERIVED THEREFROM

This application is a division of, and claims the benefit under 35 U.S.C. §120 of, U.S. application Ser. No. 11/731, 290, filed Mar. 30, 2007, which by this reference is incorporated in its entirety as a part hereof for all purposes.

This application claims the benefit of U.S. Provisional Application No. 60/787,829, filed Mar. 31, 2006, which is incorporated in its entirety as a part hereof for all purposes.

TECHNICAL FIELD

The present invention is related to the chemical synthesis of bis(meth)acrylate chiral compounds, liquid crystal compositions comprising the chiral compounds, and polymerization of the liquid crystal compositions to provide polymer networks with useful cholesteric optical properties.

BACKGROUND

Thermotropic liquid crystals are generally crystalline compounds with significant anisotropy in shape. That is, at the molecular level, they are characterized by a rod-like or disc like structure. When heated they typically melt in a stepwise manner, exhibiting one or more thermal transitions from a crystal to a final isotropic phase. The intermediate phases, known as mesophases, can include several types of smectic phases wherein the molecules are generally confined to layers; and a nematic phase wherein the molecules are aligned parallel to one another with no long range positional order. The liquid crystal phase can be achieved in a heating cycle, or can be arrived at in cooling from an isotropic phase. A comprehensive description of the structure of liquid crystals in general, and twisted nematic liquid crystals in particular is given in "The Physics of Liquid Crystals," P. G. de Gennes and J. Prost, Oxford University Press, 1995.

An important variant of the nematic phase is one wherein a chiral moiety is present, referred to as a twisted nematic or cholesteric phase. In this case the molecules are parallel to each other as in the nematic phase, but the director of molecules (the average direction of the rodlike molecules) changes direction through the thickness of a layer to provide a helical packing of the nematic molecules. The pitch of the helix is perpendicular to the long axes of the molecules. This helical packing of anisotropic molecules leads to important and characteristic optical properties of twisted nematic phases including circular dichroism, a high degree of rotary power; and the selective reflection of light, including ultraviolet, visible, and near-IR light. Reflection in the visible region leads to brilliantly colored layers. The sense of the helix can either be right-handed or left-handed, and the rotational sense is an important characteristic of the material. The chiral moiety either may be present in the liquid crystalline molecule itself, for instance, as in a cholesteryl ester, or can be added to the nematic phase as a dopant, with induction of the cholesteric phase. This phenomenon is well documented, see e.g. H. Bassler, M. M. Labes, J. Chem. Phys., 52 p 631 (1970).

There has been significant effort invested in the synthesis and polymerization methods for preparing stable polymer layers exhibiting fixed cholesteric optical properties. One approach has been to synthesize monofunctional and/or polyfunctional reactive monomers that exhibit a cholesteric phase upon melting, formulate a low melting liquid crystal composition, and polymerize the liquid crystal composition in its cholesteric phase to provide a polymer network exhibiting stable optical properties of the cholesteric phase. Use of cholesteric monomers alone, as disclosed in U.S. Pat. No. 4,637,896, provided cholesteric layers with the desired optical properties, but the polymer layers possessed relatively weak mechanical properties. Many efforts have been made to improve the physical properties and thermal stabilities by formulating twisted nematic monomer phases that are capable of crosslinking polymerizations to provide polymer networks. Crosslinking chiral monomers including bis(meth)acrylates with ether groups (—O—) linking a core chiral group to flexible spacers and polymerizable (meth)acrylates are disclosed in U.S. Pat. No. 5,780,629 and U.S. Pat. No. 6,723,395. U.S. Pat. No. 6,468,444 discloses related chiral dopants with a carbonate, —O—C(O)—O—, linking a core chiral group to a flexible spacer and polymerizable (meth)acrylates. Although the references claim ester groups (—C(O)—O—) linking the core chiral group to flexible spacers and the polymerizable (meth)acrylate, there is limited disclosure in the reference useful in relation to the teaching of how to make and use bis(meth)acrylates with aliphatic esters groups (—C(O)—O—) linking the core chiral group to flexible spacers and the polymerizable (meth)acrylates. Furthermore, there is limited disclosure in relation to their specific physical or chemical properties.

A need thus remains for a process to make chiral bis(meth)acrylates with esters linking the chiral group to a flexible spacer and the polymerizable (meth)acrylates. There is also need for chiral crosslinking monomers that can induce twisted nematic phases in nematic liquid crystals, and there is a need for polymer networks that exhibit cholesteric optical properties.

SUMMARY

One embodiment of the invention is a compound of Formula (I):

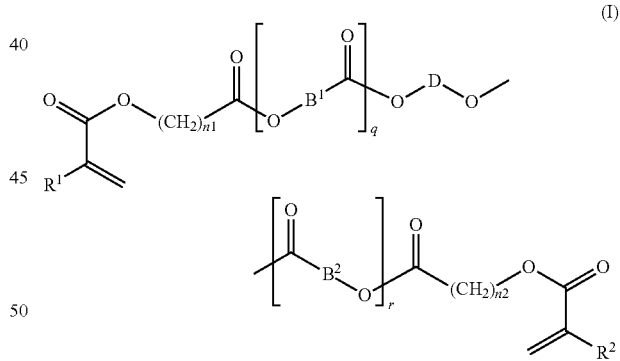

wherein $R^1$ and $R^2$ are each independently selected from the group: H, F, Cl and $CH_3$; n1 and n2 are each independently integers 3 to 20; q and r are each independently integers 0, 1 or 2, with the proviso that q+r is $\geq 1$; D is a divalent chiral radical selected from the group:

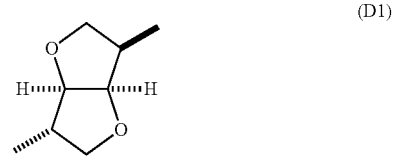

(D1)

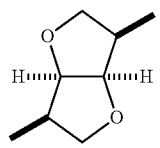
(D2)

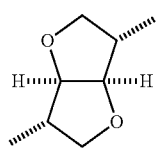
(D3)

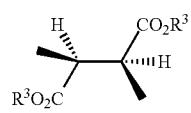
(D4)

wherein $R^3$ is a C1 to C6 straight or branched chain alkyl group; and each $B^1$ and $B^2$ is a divalent radical independently selected from the group: $R^4$-substituted-1,4-phenyl, wherein $R^4$ is H, —$CH_3$ or —$OCH_3$; 2,6-naphthyl; and 4,4'-biphenyl; wherein when q+r=3, at least one of $B^1$ and $B^2$ is $R^4$-substituted-1,4-phenyl; and when q+r=4, at least two of $B^1$ and $B^2$ are $R^4$-substituted-1,4-phenyl.

Another embodiment of the invention is a polymerizable liquid crystal composition comprising at least one compound of Formula (I).

Another embodiment of the invention is a polymer network derived from polymerization of the polymerizable liquid crystal composition comprising at least one compound of Formula (I). The polymer network is useful as an optical element or as a pigment.

Another embodiment of the invention is a process for making the compounds as described by Formula (I).

DETAILED DESCRIPTION

The terms (meth)acrylate salt, (meth)acrylate ester, (meth)acrylate acid, and the like, herein encompass materials and moieties comprising: methacrylate, for instance wherein $R^1$ and/or $R^2$ is methyl; acrylate, wherein $R^1$ and/or $R^2$ is H; chloroacrylate, wherein $R^1$ and/or $R^2$ is Cl; and fluoroacrylate, wherein $R^1$ and/or $R^2$ is F; unless specifically defined otherwise.

The term "twisted nematic phase", "cholesteric phase" and "chiral nematic" herein are synonymous.

One embodiment of the invention is a compound of Formula (I):

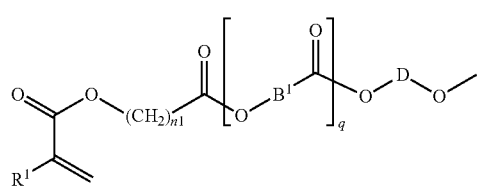
(I)

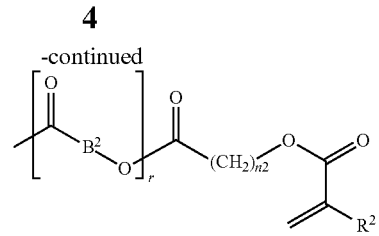

wherein $R^1$ and $R^2$ are each independently selected from the group: H, F, Cl and $CH_3$; n1 and n2 are each independently integers 3 to 20; q and r are each independently integers 0, 1 or 2, with the proviso that q+r is $\geq 1$; D is a divalent chiral radical selected from the group:

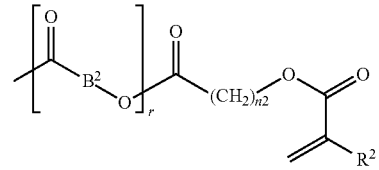
(D1)

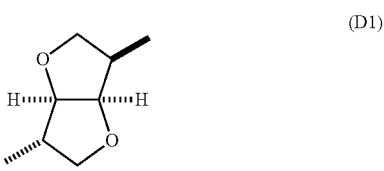
(D2)

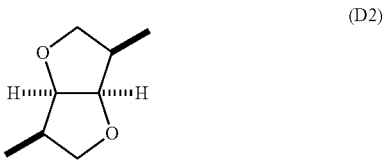
(D3)

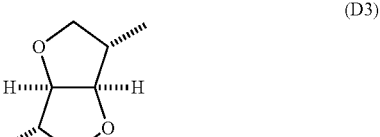
(D4)

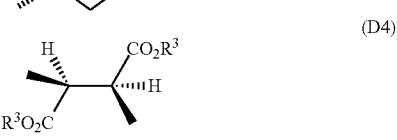

wherein $R^3$ is a C1 to C6 straight or branched chain alkyl group; and each $B^1$ and $B^2$ is a divalent radical independently selected from the group: $R^4$-substituted-1,4-phenyl, wherein $R^4$ is H, —$CH_3$ or —$OCH_3$; 2,6-naphthyl; and 4,4'-biphenyl; wherein when q+r=3, at least one of $B^1$ and $B^2$ is $R^4$-substituted-1,4-phenyl; and when q+r=4, at least two of $B^1$ and $B^2$ are $R^{11}$-substituted-1,4-phenyl.

In the phrase "each $B^1$ and $B^2$ is a divalent radical independently selected from the group:", when q=2, the two $B^1$ units are selected independently, that is they may be the same or different; and when r=2, the two $B^2$ units are selected independently, that is they may be the same or different. In addition, a C1-C6 group may be any one or more of $C_1$, $C_2$, $C_3$, $C_4$, $C_5$, or $C_6$.

A preferred embodiment of the invention is a composition of Formula (I) wherein $R^1$ and $R^2$ are independently selected from H and $CH_3$, and more preferably, $R^1$ and $R^2$ are H. Preferably n1 and n2 are, independently, integers 3 to 10. Preferably the divalent chiral moiety D is selected from the group of Formulae (D1), (D2) and (D3).

Another preferred embodiment of the invention is a composition of Formula (I) wherein q and r is equal 1, and particularly preferred is a composition, wherein q and r is equal to 1 and $B^1$ and $B^2$ are $R^4$-substituted-1,4-phenyl.

Particularly favored compositions are wherein D is equal to (D1) and $B^1$ and $B^2$ are $R^4$-substituted-1,4-phenyl, or 4,4'- biphenyl. Other particularly favored compositions are wherein D is equal to (D2) and $B^1$ and $B^2$ are $R^4$-substituted-1,4-phenyl.

One embodiment of this invention is a process for providing the compound of Formula (I), which process may be distinguished from previous information concerning synthetic methods related to the preparation of similar types of compounds. For example, although U.S. Pat. No. 5,780,629 discloses in general terms materials including those of Formula (I), there is limited disclosure useful in relation to how to make the specific compounds of Formula (I) comprising ester moieties linking $B^1$ and $B^2$ to the spacer groups and the (meth)acrylate groups. The available disclosure is directed essentially at the synthesis of compounds wherein ether (—O—) moieties link $B^1$ and $B^2$ to the spacer groups. As will be shown in the examples below, U.S. Pat. No. 5,780,629 has limited useful disclosure in relation to providing the compound of Formula (I).

This invention thus provides, in the aforementioned embodiment, a process for preparing the compound of Formula (I) by: (a) providing a chiral organic diol, such as that from which the radical D is obtained; (b) reacting the chiral organic diol with one or more functionalized alkyl acids or acid halide(s) of the Formula (II):

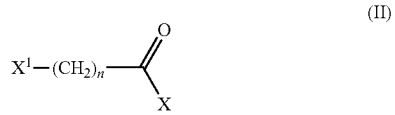

(II)

wherein X is Cl, Br or OH; $X^1$ is selected from the group: Cl, Br, I, —OMs (wherein Ms is methanesulfonyl), —OTs (wherein, Ts is toluenesulfonyl), and —OTf (wherein Tf is trifluoromethanesulfonyl); and n is an integer equal to 3 to 20; in a first reaction solvent at a first reaction temperature to provide one or more polyfunctionalized ester(s) and a first spent reaction mixture; (c) reacting the one or more polyfunctionalized ester(s) with a (meth)acrylate salt in the presence of a phase transfer catalyst, and a second reaction solvent at a second reaction temperature; to provide one or more poly (meth)acrylate ester(s) and a second spent reaction mixture. The poly(meth)acrylate ester(s) may be alkyl and/or aryl ester(s). Preferably, the process step (b) further comprises the uses of a base, and when X is OH, further comprises the use of a carbodiimide dehydrating agent. Step (c) preferably further comprises the use of one or more radical inhibitors.

Preferred functionalized alkyl acid halide(s) of the Formula (II) are acid chlorides (X=Cl) wherein $X^1$ is Br. A sufficient amount of the functionalized alkyl acid halide(s) preferably is about 1.8 to about 2.5 equivalents, and more preferably about 2.0 to 2.2 equivalents, based on the amount of the chiral organic diol. In a preferred embodiment, in step (b) the one or more functionalized alkyl acid halides(s) comprises two functionalized alkyl acid halide(s) in a molar ratio of about 0.05:1 to 1:1, or two or more functionalized alkyl acid halide(s); and said step (b) provides a mixture of at least three polyfunctionalized alkyl ester(s). This process, or derivations thereof using three or more polyfunctionalized alkyl acid halide(s), is a convenient and preferred process to provide complex mixtures of the compounds of the invention.

The first reaction solvent can be any solvent known in the art to be useful in performing acid halide condensations with alcohols, including alkyl ethers, such as THF, dioxane, dimethoxyethane; alkyl esters such as ethyl acetate and butyl acetate; hydrocarbons such as xylenes, and toluene; halogenated hydrocarbons such as 1,2-dichloroethane and dichloromethane. A preferred first reaction solvent is THF.

The (meth)acrylate salt useful in step (c) can be derived from neutralization of the corresponding (meth)acrylate acid including methacrylic acid, acrylic acid, 2-chloroacrylic acid, and 2-fluoroacrylic acid. The base used in the neutralization can be an alkali metal base, for instance, potassium carbonate and bicarbonate, sodium carbonate and bicarbonate; lithium carbonate and bicarbonate, and cesium carbonate and bicarbonate; to provide an alkali metal (meth)acrylate salt. The base can be an alkali earth metal base, for instance, magnesium, calcium or barium carbonate; to provide an alkali earth metal (meth)acrylate salt. The base also can be an amine base and particularly a hindered amine base such as a tertiary aliphatic, aromatic or heterocyclic amine as described above; to provide an ammonium (meth)acrylate salt. Preferred (meth)acrylate salts for step (c) are selected from the group: potassium (meth)acrylate, sodium (meth)acrylate, and ammonium (meth)acrylates selected from the group: triethylammonium, diisopropylethylammonium, and 2,6-dimethylpyridinium salts.

The (meth)acrylate salt can be provided from commercial sources; it can be prepared in a separate process step and used directly or purified by one or more methods known in the art such as washing, filtering, drying, recrystallizing, or precipitating the salt; or it can be made in situ by neutralization of a (meth)acrylate acid with a base. A preferred embodiment of the invention is wherein the (meth)acrylate salt is provided by mixing (meth)acrylic acid and an alkali metal carbonate selected from the group: potassium hydrogen carbonate and potassium carbonate; in a molar ratio of about 1:1 to about 1:5, respectively, in said second reaction solvent.

In a preferred process, the amount of (meth)acrylate salt to be used is about 2.0 about 10.0 equivalents per equivalent of the polyfunctionalized alkyl ester(s). Preferably the (meth)acrylate salt is an acrylate salt.

The phase transfer catalyst used in step (c) is a substance which, being at least partly present in or wetted by a first (usually organic) phase, promotes reaction between a reactant in the first phase and a reactant which it transfers to the first phase from a second phase, usually an aqueous or a solid phase. After reaction, the phase transfer catalyst is released for transferring further reactant. Suitably the phase transfer catalyst is a quaternary ammonium or phosphonium salt preferably containing bulky organic groups, usually alkyl or aralkyl groups, to make it soluble in the organic phase. It is preferred that the phase catalyst is a tetraalkyl or aralkyl (e.g. benzyl) trialkyl ammonium or phosphonium salt in which the total number of carbon atoms attached to each nitrogen or phosphorus atom is at least 4. It is especially preferred that the number should be in the range of from 16 to 40. Other substances suitable for use herein as the phase transfer catalyst include those reviewed by E. V. Dehmlow in Angewante Chemie, (International Edition), 13, 170 (1974).

Examples of quaternary ammonium salts are: cetyltrimethylammonium bromide, dicetyldimethylammonium chloride, octyltributylammonium bromide, trioctylmethylammonium chloride (available as Aliquat™ 336), benzyldimethyllaurylammonium chloride, benzyltriethylammonium chloride, dilauryldimethylammonium chloride, tetrabutylammonium bromide, tetrabutylammonium hydrogen sulfate and tetrabutylammonium iodide. Examples of quaternary phosphonium salts are cetyltripropylphosphonium bromide and triphenylethylphosphonium bromide. Other phase transfer catalysts that may be suitable include crown ethers and polyethylene glycol variants. The phase transfer catalyst may be present in an amount ranging from 0.001 to 0.5 mole equivalents, and preferably 0.1-0.5 equivalents, of the polyfunctionalized alkyl ester(s). A preferred phase transfer catalyst is selected from the group: tetrabutylammonium iodide, tetrabutylammonium bromide; and tetraheptyl ammonium bromide; and crown ethers selected from the group: 18-crown-6, CAS No. [17455-13-9]; benzo-18-crown-6, CAS No. [14078-24-9]; 15-crown-5, CAS No. [33100-27-5]; and benzo-15-crown-5, CAS No. [140-44-3].

The second reaction solvent can be any solvent known in the art to be useful in performing nucleophilic displacement of —$X^1$ with a (meth)acrylate salt. However, there is a preference for particular second reaction solvents that are aprotic in structure, and have a dipole moment of about 3.5 or less. By aprotic in structure we mean the solvents are devoid of active hydrogens such as hydroxyl or acid functionality. Solvents having these characteristics provide high rates of conversion of the polyfunctionalized alkyl ester(s) to product while maintaining a very low level of undesired ester cleavage products. Preferred second reaction solvents include those selected from the group: alkyl ethers including tetrahydrofuran, dioxane and dimethoxyethane; ketones including acetone and 2-butanone; alkyl esters including butyl acetate and ethyl acetate; and acetonitrile. In a preferred embodiment, the second reaction solvent may be the first spent reaction mixture.

The first reaction temperature and second reaction temperature are reaction temperatures that give a reasonable rate of reaction with a minimum of by-products. The first reaction temperature generally is between −30° C. and about 50° C., and preferably about 0° C. to about room temperature (RT, e.g. 25° C.). The second reaction temperature is generally about RT to about 120° C., and preferably about 50° C. to about 100° C.

When a base is used in step (b), it can include an inorganic base, for instance, alkali metal and alkali earth metal hydroxide, carbonate and bicarbonate; or an organic base such as an amine base that has at least two aliphatic groups, or that in which the N atom is in a cycloaliphatic or aromatic ring, substituted in a manner that induces steric crowding around the N atom. Typically the amine base will be of low water solubility and have a $pK_a$ of the conjugate acid of about 10. Thus, it may be a heteroaromatic base such as pyridine or a substituted pyridine, for example 2,6-dimethylpyridine; or it may be a secondary amine, providing it is sufficiently sterically hindered. An example of a suitable secondary amine is 2,2,6,6-tetramethyl-piperidine. Preferably, however, it is a tertiary amine of formula $R^{13}R^{14}R^{15}N$ wherein $R^{13}$, $R^{14}$ and $R^{15}$ are independently $C_{1-10}$ alkyl groups or $C_{3-6}$ cycloalkyl groups. The alkyl groups may be straight or branched chain. Examples are methyl, ethyl, iso-propyl, n-propyl, n-butyl, sec-butyl and tert-butyl. Suitable tertiary amines of formula $R^{13}R^{14}R^{15}N$ are, for example, N,N-diisopropylethylamine, N,N-dimethylaniline, triethylamine, t-butyldimethylamine, N,N-diisopropylmethylamine, N,N-diisopropylisobutylamine, N,N-diisopropyl-2-ethylbutylamine, tri-n-butylamine. Preferred are amine bases selected from the group: triethylamine, diisopropylethylamine, tributylamine, pyridine, and 2,6-dimethylpyridine; and triethylamine is most preferred. The base is preferably present in an amount of about 0.8 to about 5 equivalents per equivalent of the functionalized alkyl acid halide(s).

When an amine base is used in step (b), a by-product of the reaction is an amine salt such as an amine hydrochloride. In a preferred embodiment the amine salt is removed from the first spent reaction mixture by, for instance, filtering the reaction mixture. This is a convenient and preferred process wherein the second reaction solvent can include the first reaction solvent. In another embodiment the one or more polyfunctionalized alkyl ester(s) provided by step (b) can be separated from the first spent reaction mixture by a variety of methods known in the art. Preferred methods include any one or more of the steps: filtering the amine salt by-product; precipitating the reaction mixture into water and filtering; partitioning the reaction mixture with water and/or organic solvents; washing with reaction mixture with water; drying the reaction mixture with a drying agent; removal of solvent by evaporation; chromatography, crystallization and/or recrystallization of the one or more polyfunctionalized alkyl ester(s); and washing the crude product with one or more solvents which selectively remove byproducts without dissolving the one or more polyfunctionalized alkyl ester(s).

A carbodiimide dehydrating agent, when used in step (b), can be any diimide commonly used in coupling acids with alcohols and phenols. A preferred carbodiimide for step (b) is dicyclohexylcarbodiimide.

A radical inhibitor, when used in step (c), can be any radical inhibitor known to inhibit radical polymerization reactions of (meth)acrylate groups including 2,6-di-tert-butylphenol, 2,6-di-tert-butyl-4-methylphenol, 2,6-di-tert-butyl-4-ethylphenol, 2-methyl-6-tert-butylphenol, 2,4,6-tri-tert-octylphenol, 2,4-dimethyl-6-tert-butylphenol, 2-tert-butyl-6-(α-methylbenzyl)phenol, 2,4-di-tert-octylphenol, 2,6-di-tert-butyl-4-methoxyphenol, 2,6-di-tert-octyl-4-decoxyphenol, 2-tert-butyl-4-chlorophenol, 2,6-di-tert-butyl-4(N,N'-dimethylaminomethylphenol), 2,2'-methylene-bis(4-methyl-6-tert-butylphenol), 2,2'-methylene-bis(4-ethyl-6-tert-butylphenol), 2,2'-methylene-bis(4-methyl-6-nonylphenol), 4,4'methylenebis(2,6-di-tert-butylphenol), 4,4'-bis(2,6-di-tert-butylphenol), 4,4'-bis(2-methyl-6-tert-butylphenol), 4,4'-isopropylidenebis(2,6-di-tert-butylphenol), 1,4-hydroquinone, 4-methoxyphenol and the like; phosphorus compounds, such as tri(nonylphenyl)phosphate, tridecyl phosphite, and the like; naphthol-based compounds, such as 1,2-dihydroxynaphthalene, 1-amino-2-naphthol, 1-nitro-2-naphthol, etc.; amine compounds, such as trimethylamine, phenyl-β-naphthylamine, p-phenylenediamine, mercaptoethylamine, N-nitrosodimethylamine, benzotriazoles, phenothiazine, halo-dihydro-2,2,4-trimethylquinone, and the like; or sulfur compounds, such as dilaurylthio dipropionate, dilauryl sulfide, and 2-mercaptobenzimidazole. The above list is not intended to be exhaustive; numerous classes of compounds that inhibit formation of radicals in organic materials are well known, and can be used in the practice of the present process. The radical inhibitor can be a single compound, or a mixture of combination of such compounds. The preferred radical inhibitors are hindered phenols selected from the group: 2,6-di-tert-butyl-4-methylphenol, phenothiazine, and tridecyl phosphate.

In another embodiment the process further comprises separating the one or more poly(meth)acrylate ester(s) provided by step (c) from the second spent reaction mixture. This can be by a variety of methods known in the art including any one or more of the steps: filtering the second spent reaction mixture; precipitating the reaction mixture into water and filtering; partitioning the reaction mixture with water and/or organic solvents; washing the reaction mixture with water; drying the reaction mixture with a drying agent; removal of solvent by evaporation; chromatography, crystallization and/or recrystallization of the one or more poly(meth)acrylate ester(s); and washing the crude product with one or more solvents which selectively remove byproducts without dissolving the one or more polyfunctionalized alkyl ester(s).

In a preferred embodiment using the process described above, compounds of Formula (I) wherein q and r are 1; and $B^1$ and $B^2$ are $R^4$-substituted-1,4-phenyl radicals can be made from chiral diester diols (IIIa-d):

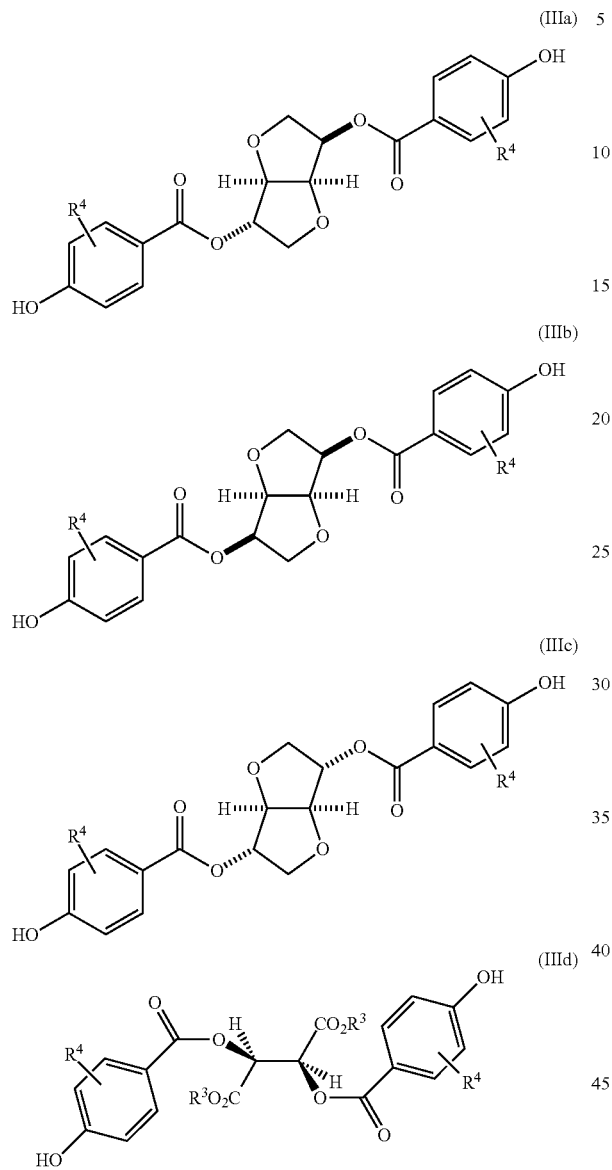

In another preferred embodiment using the process described above, compounds of Formula (I) wherein q is 1 and r is 0; and $B^1$ and $B^2$ are $R^4$-substituted-1,4-phenyl radicals can be made from chiral ester diols (IVa-e):

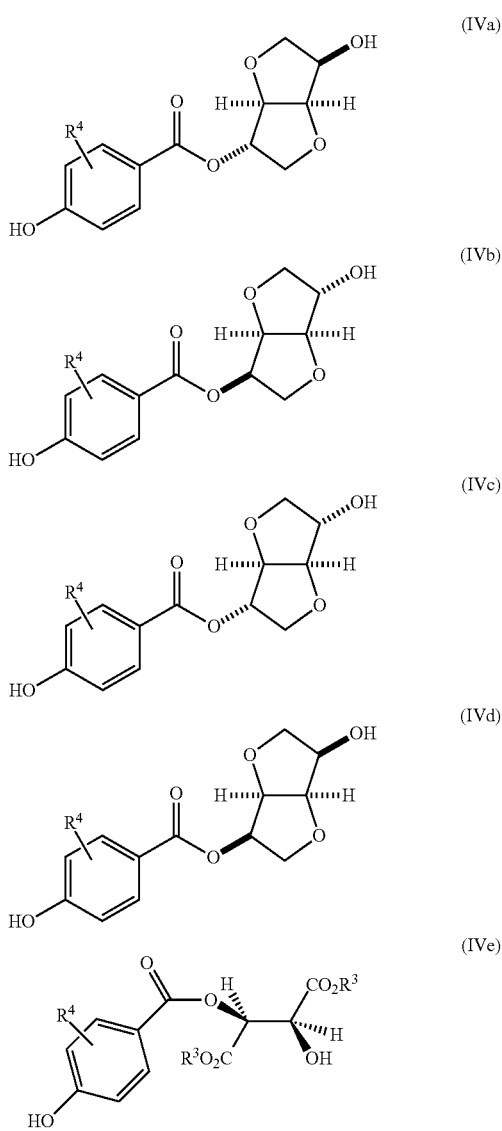

The diester diols (IIIa-d) are available by esterification of respective chiral diols: 1,4:3,6 dianhydro-D-sorbitol, CAS No. [652-67-5]; 1,4:3,6 dianhydro-D-mannitol, CAS No. [643-74-7]; 1,4:3,6 dianhydro-L-iditol, CAS No. [24332-71-6]; diethyl L-tartrate, CAS No. [87-91-2]. These chiral diols are available commercially from Aldrich Chemical Co. The diester diols (IIIa-c) are readily prepared by heating the chiral diols with two or more equivalents of hydroxy acid in the presence of an acid catalyst with azeotropic removal of water. Chiral diol (IIId) can be made by esterification of diethyl L-tartrate with 4-benzyloxybenzoyl chloride in the presence of a base, followed by hydrogenation to cleave the benzyl protecting group. Other compounds of Formula (I), wherein q and r equal 1, can be made in a similar manner using diester diols related to (IIIa-c) wherein the carboxylate group is derived from 6-hydroxy-2-napthalene carboxylic acid and 4'-hydroxy-4-biphenyl carboxylic acid.

The ester diols (IVa-d) are available by mono-esterification of respective chiral diols. U.S. Pat. No. 6,468,444, for instance, discloses the synthesis of material of formula (IVd) wherein $R^4$ is H, the monoester of isomannitol, using an equivalent amount of 4-hydroxybenzoic acid and isomannitol in refluxing xylene in the presence of p-toluenesulfonic acid. Chiral diol (IVe) can be made by selective mono-esterification of diethyl L-tartrate with 4-benzyloxybenzoyl chloride in the presence of a base, followed by hydrogenation to cleave the benzyl protecting group.

Other compounds of Formula (I), wherein q is 1 and r is 0, can be made in a similar manner using ester diols related to (IVa-e) wherein the carboxylate group is derived from 6-hydroxy-2-napthalene carboxylic acid and 4'-hydroxy-4-biphenyl carboxylic acid.

Another embodiment of the invention is a process for preparing the compounds of Formula (I) wherein q and/or r is equal to 2. The process comprises (a) providing one or more polyol(s) selected from the group: Formulae (IIIa-d) and (IVa-e); and (b) reacting the polyol(s) with a sufficient amount of one or more (meth)acrylate aryl acids or acid halides of the Formula (Va-c):

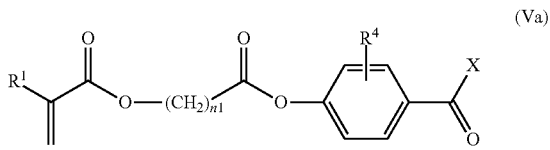
(Va)

to induce chirality of a nematic phase to provide a twisted nematic phase. Useful twisted nematic phases can be provided by mixing the chiral dopants at about 0.5 to about 30 wt % based on the total nematic mixture. A wide variety of polymerizable and nonpolymerizable liquid crystals can be used in the polymerizable liquid crystal compositions of the invention including in those disclosed in Makromol. Chem. 190, 2255-2268 (1989); Macromolecules, 1988, 31, 5940; Makromol. Chem. 192, 59-74 (1991); J. Polym. Sci.: Part A: Polym. Chem., Vol. 37, 3929-3935 (1999); and Makromol. Chem. 190, 3201-3215 (1989). Additional polymerizable monomers useful in liquid crystal compositions are disclosed in U.S. Pat. No. 5,833,880, DE 4,408,170, EP 261,712, EP 331,233 B1, EP 397,263 B1, and WO 1998/047979, hereby incorporated by reference. A preferred group of polymerizable monomers are those of Formula (VI):

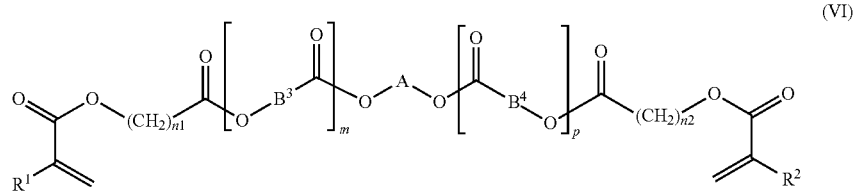
(VI)

-continued

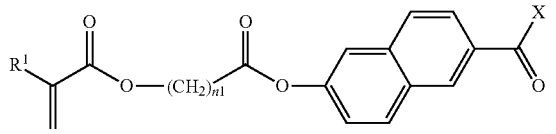
(Vb)

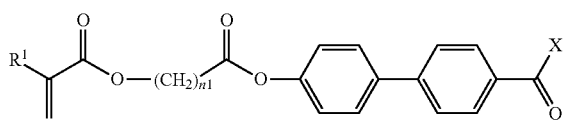
(Vc)

wherein X is Cl, Br, or OH, n1 is an integer 3-20; $R^1$ and $R^4$ are as described above; and a first reaction solvent at a first reaction temperature to provide one or more poly(meth)acrylate alkanoate ester(s) of Formula (I) wherein q and/or r=2. Preferably step (b) includes a base and one or more radical inhibitors as described above; and when X is OH, further comprises a carbodiimide dehydrating agent. The process is suitable for esterification of polyol(s) related to (IIIa-d) and (IVa-e) wherein the carboxylate group is derived from 6-hydroxy-2-napthalene carboxylic acid and 4'-hydroxy-4-biphenyl carboxylic acid, within the limits of the provisos disclosed for compounds of Formula (I).

The preparation of (meth)acrylate acid halides of Formula (V) is exemplified in the examples. In the processes described above, the contents of the reaction mixture are used in at least an amount that is sufficient to enable the reaction to proceed to provide the stated product at a rate and with a yield that is commercially useful.

Compounds of Formula (I) are useful in polymerizable liquid crystal compositions (i.e. mixtures), also of the invention. Compounds of Formula (I) are useful as chiral dopants wherein $R^1$ and $R^2$ are independently selected from the group: H, F, Cl and $CH_3$; n1 and n2 are, independently, integers 3 to 20; m and p are, independently, integers 0 or 1; A is a divalent radical selected from the group:

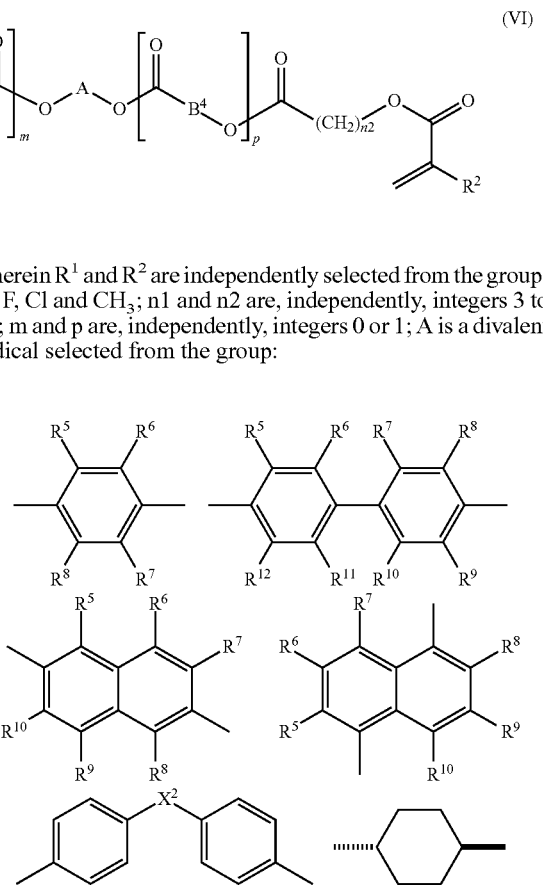

wherein $R^5$-$R^{12}$ are independently selected from the group: H, C1-C8 straight or branched chain alkyl, C1-C8 straight or branched chain alkyloxy, F, Cl, phenyl,
—C(O)$CH_3$, CN, and $CF_3$; $X^2$ is a divalent radical selected from the group: —O—, —($CH_3$)$_2$C—, and —($CF_3$)$_2$C—; and each $B^3$ and $B^4$ is a divalent radical independently selected from the group: $R^4$-substituted-1,4-phenyl, wherein $R^4$ is H, —$CH_3$ or —$OCH_3$; 2,6-naphthyl; and 4,4"-biphenyl; with the proviso that when m+p is equal to 3 or 4, at least two of $B^3$ and $B^4$ are $R^4$-substituted-1,4-phenyl. In addition, a C1-C8 group may be any one or more of $C_1$, $C_2$, $C_3$, $C_4$, $C_5$, $C_6$, $C_7$ or $C_8$. Preferred polymerizable liquid crystal compositions of the invention have a twisted nematic phase below 120° C.

The synthesis of compounds of Formula (VI) and liquid crystal mixtures thereof is described in U.S. Provisional Application No. 60/788,525, filed Mar. 31, 2006, and entitled "Liquid Crystal Compositions, Polymer Networks Derived Therefrom and Process for Making the Same", which is incorporated in its entirety as a part for all purposes.

The liquid crystal compositions of the invention are useful in preparing polymer networks that exhibit the fixed optical properties of twisted nematic polymer networks. The polymer network of the invention is one or more polymerized layer(s) comprising a liquid crystal composition that include: polymerized films, coatings, castings and prints; including patterned, unpatterned, variable and nonvariable optical properties; that can be made by a wide variety of methods as disclosed, for instance, in U.S. Pat. Nos. 4,637,896, 6,010,643 and 6,410,130, all hereby incorporated by reference.

In particular, one preferred method for making a polymer network comprises: providing a polymerizable twisted nematic mixture, in the form of a twisted nematic or isotropic phase, with a polymerization initiator, preferably a radical initiator; applying the twisted nematic mixture to one or more substrates, optionally the substrate(s) comprises an alignment layer, to provide a layer of the twisted nematic mixture; optionally treating the layer to provide a desired twisted nematic phase; and polymerizing the twisted nematic phase, preferably by exposing the twisted nematic phase to actinic radiation. Actinic radiation includes heat, microwave radiation, UV and visible light, and electron beam and other radiation.

The liquid crystal compositions of various embodiments of the invention can include a radical initiator, and preferably the radical initiator is a photoinitiator useful in conducting photochemical polymerizations. Photochemical polymerizations can include customary commercial photoinitiators including, for example, isobutyl benzoin ether, 2,4,6-trimethylbenzoyl-diphenylphosphine oxide, and/or 1-hydroxycyclohexyl phenyl ketone. For curing by electron beams, such initiators are not required. Applying the twisted nematic mixture can be accomplished by any method that gives a uniform layer, or if desired, a patterned or non-uniform layer. Coating, including rod-coating, extrusion coating, gravure coating and spin-coating, spraying, printing, blading, knifing, or a combination of methods, can be used. Substrates can be pre-coated with alignment layers: polymers that are applied to substrates and mechanically buffed with a rubbing clothe or optically aligned with polarized light. Useful polyimide alignment layers are disclosed in U.S. Pat. No. 6,887,455. Alignment of twisted nematic phases by coating of dilute liquid crystal mixtures is disclosed in U.S. Pat. No. 6,410,130.

The ability of twisted nematic phases to selectively reflect light in the infrared, visible or ultraviolet region is useful in many applications. When the propagation direction of plane polarized or unpolarized light is along the helical axis of the twisted nematic layer, the wavelength of maximum reflection, $\lambda_o$, is governed by the equation
$\lambda_o = n_a p$, wherein $n_a$ is the average of $n_o$ and $n_e$, and $n_o$ and $n_e$ are defined as the ordinary and extraordinary refractive indices respectively, of the twisted nematic phase measured in the propagation direction and p is the pitch of the helix (the distance the helix takes to repeat itself). Light outside the vicinity of $\lambda_0$ is essentially unaffected in transmission. For light with a wavelength in the vicinity of wavelength $\lambda_0$ the twisted nematic phase exhibits selective reflection of the light such that approximately 50% of the light is reflected and approximately 50% of the light is transmitted, with both the reflected and transmitted beams being substantially circularly polarized. A right handed helix reflects right handed circularly polarized light and transmits left handed circularly polarized light. The bandwidth $\Delta\lambda$ of this reflected wavelength band centered about $\lambda_0$ can be determined by the formula $\Delta\lambda = \lambda_0 \cdot \Delta n / n_a$, where $\Delta n = n_e - n_o$, reflecting the birefringence present in liquid crystal materials. The pitch p can be tuned effectively by manipulating the amount of chiral dopant, the twisting power of the dopant and selection of the nematic materials. The pitch is sensitive to temperature, unwinding or tightening with a change in temperature; to electric fields, dopants, and other environmental considerations. Thus, in the twisted nematic phase, manipulation of the pitch, and thus the wavelength of maximum reflection, can be accomplished with a wide variety of tools. Furthermore, the bandwidth $\Delta\lambda$ of the reflected wavelength band also can be manipulated as disclosed in U.S. Pat. No. 5,506,704 and U.S. Pat. No. 5,793,456.

The polymer networks of the invention can be made either flexible or brittle depending on crosslinking. The brittle films can be flaked and the flakes used as pigments in a variety of inks or paints for use in cosmetics and automobile paint. The films can be combined with other pigments or pigment layers, for instance black layers that act to enhance the brilliance of the reflected light.

The polymer networks of the invention are useful as optical elements or components of an optical element. An optical element is any film, coating or shaped object that is used to modify the characteristics of light. The modifications produced by optical elements include changes in the intensity of light through changes in transmission or reflectivity, changes in wavelength or wavelength distribution, changes in the state of polarization, changes in the direction of propagation of part or all of the light, or changes in the spatial distribution of intensity by, for example, focusing, collimating, or diffusing the light. Examples of optical elements include linear polarizers, circular polarizers, lenses, mirrors, collimators, diffusers, reflectors and the like. One specific example of an optical element is a layer of a cholesteric polymer network of the invention that reflects light within the vicinity of $\lambda_o$, employed in a window structure.

An optical element prepared from a polymer network as provided by this invention may be used as a component in a multilayer laminate, one form of which may be a laminated article. In one embodiment, the optical element may be provided in the form of a sheet that has a thickness of greater than about 10 mils (0.25 mm), or about 20 mils (0.50 mm) or greater, where the total thickness of all components from which the laminate is composed may be a thickness of about 30 mils (0.75 mm) or greater to ensure adequate penetration resistance commonly regarded as a feature of safety laminates. Polymeric sheets useful for such purpose may be formed by any suitable process such as extrusion, calendaring, solution casting or injection molding.

A polymeric sheet to be used as an interlayer within a laminate may have a roughened surface to effectively allow most of the air to be removed from between the surfaces of the laminate during the lamination process. This may be accomplished, for example, by mechanically embossing the sheet after extrusion, as described above, or by melt fracture during extrusion of the sheet and the like. This rough surface is only temporary and particularly functions to facilitate deairing during laminating after which it is melted smooth from the elevated temperature and pressure associated with autoclaving and other lamination processes.

In an embodiment where the optical element to be used in a laminate is a polymeric film, the film may be treated to enhance the adhesion to a coating or to a polymeric sheet or both. This treatment may take any suitable form known such as adhesives, primers, such as silanes, flame treatments, plasma treatments, electron beam treatments, oxidation treatments, corona discharge treatments, chemical treatments, chromic acid treatments, hot air treatments, ozone treatments, ultraviolet light treatments, sand blast treatments, solvent treatments, and the like and combinations thereof. A film suitable for use herein as an optical element may have a thickness of about 10 mils (0.25 mm) or less, or a thickness of between about 0.5 mils (0.012 millimeters (mm)), to about 10 mils (0.25 mm), or a thickness of about 1 mil (0.025 mm) to about 5 mils (0.13 mm).

In a further embodiment, a process to produce a multilayer laminate according to this invention provides a polymeric sheet laminated to a polymeric film that is coated with the twisted nematic liquid crystal layer. The polymeric sheet may be lightly bonded to the film with the twisted nematic liquid crystal through a nip roll bonding process. The components may be heated to a temperature sufficient to promote temporary fusion bonding, i.e., to cause the surfaces of the polymeric sheet or the polymeric film to become tacky. Suitable temperatures are within the range of about 50° C. to about 120° C., with the preferred surface temperatures reaching about 65° C. The film with the twisted nematic liquid crystal is fed along with the polymeric sheet through nip rolls where the two layers are merged together under moderate pressure to form a weakly bonded laminate. Generally the bonding pressure will be within the range of about 10 psi (0.7 kg/sq cm), to about 75 psi (5.3 kg/sq cm), and is preferably within the range of about 25 psi (1.8 kg/sq cm), to about 30 psi (2.1 kg/sq cm). After bonding, the laminate is passed over a series of cooling rolls which ensure that the laminate taken up on a roll is not tacky. Laminates made through this process will have sufficient strength to allow handling by laminators who may produce further laminated articles, such as glass laminates, which encapsulate this laminate.

A multi-layer laminate may also be formed by an autoclave processes wherein a glass sheet, an interlayer composed of a polymeric sheet, a polymeric film with the twisted nematic liquid crystal (either in the form of a coated layer or of a film), a second polymeric sheet, and a second glass sheet are laminated together under heat and pressure and a vacuum (for example, in the range of about 27-28 inches (689-711 mm) Hg), to remove air.

In addition to a layer of a twisted nematic liquid crystal, whether as a polymeric sheet or as a polymeric film (either in the form of a coated layer or a film), a multilayer laminate as provided by this invention may include additional layers, such as other polymeric sheets, other coated or uncoated polymeric films, half-wave plates and absorptive layer. The additional layers may be glass or rigid transparent plastic sheets, such as, for example, polycarbonates, acrylics, polyacrylates, cyclic polyolefins, such as ethylene norbornene polymers, metallocene-catalyzed polystyrenes and the like and combinations thereof. Metal or ceramic plates may also be suitable, if transparency is not required for the laminate. The term "glass" is meant to include not only window glass, plate glass, silicate glass, sheet glass, and float glass, but also includes colored glass, specialty glass which includes ingredients to control, for example, solar heating, coated glass with, for example, sputtered metals, such as silver or indium tin oxide, for solar control purposes and other specialty glasses. The type of glass to be selected for a particular laminate depends on the intended use.

An absorptive layer may also comprise part of a laminate as provided herein. The absorptive layer may be in the form of a discrete film. In other embodiments the absorptive layer may be in the form of a coating on one or more of the twisted nematic liquid crystal layers, the polymeric sheets, the polymeric films and the rigid sheets. In still other embodiments the absorptive layer may be incorporated into one or more of the twisted nematic liquid crystal layers, the polymeric sheets, the polymeric films and the rigid sheets.

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Thermal transitions are given in degrees Centigrade. The following notations are used to describe the observed phases: K=crystal, N=nematic, S=smectic, TN*=twisted nematic, X=unidentified phase, I=isotropic, P=polymerized. The thermal transitions and phase assignments were made with differential scanning calorimetry and hotstage optical microscopy. Unless stated otherwise, phase behavior is reported for the first heating. The following abbreviations are used in the examples: THF=tetrahydrofuran, TEA=triethylamine, RT=room temperature. Unless noted otherwise, the phase behavior refers to the first heating cycle.

The synthesis of liquid crystal compounds of formula (VI) that are used in illustrating a chiral liquid crystal composition and polymer network of various embodiments the invention are described below.

Compound 3, a liquid crystal monomer is made in the following manner:

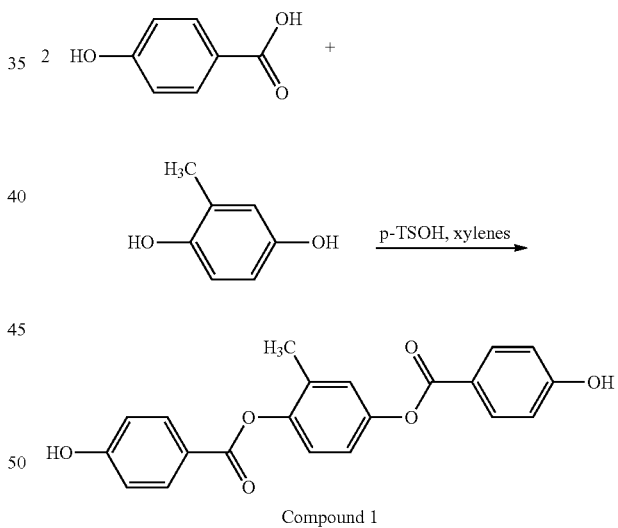

Compound 1

A mixture of 240.0 g 4-hydroxybenzoic acid, 100.2 g methylhydroquinone, 6 g p-toluenesulfonic acid, and 1500 mL xylenes in a flask equipped with a Dean-Stark trap, condenser and mechanical stirrer, was heated to reflux under a nitrogen atmosphere for a total of 26 h. Additional p-toluenesulfonic acid (6.0 g portions) was added after 8 and 18 h after cooling the reaction mixture RT. The final reaction mixture was cooled to RT, the solids collected and washed with hexanes. The solids were slurried with hot acetone (600 mL) and cooled to RT, collected and dried to provide Compound 1. $^1$H NMR (DMSO-$d_6$, 500 MHz) δ 2.16 (s, 3H), 6.93 (d, J=8.8 Hz, 2H), 6.95 (d, J=8.8 Hz, 2H), 7.13 (m, 1H), 7.23 (m, 2H), 7.99 (d, J=8.8 Hz, 2H), 8.02 (d, J=8.8 Hz, 2H), 10.51 (s, 2H).

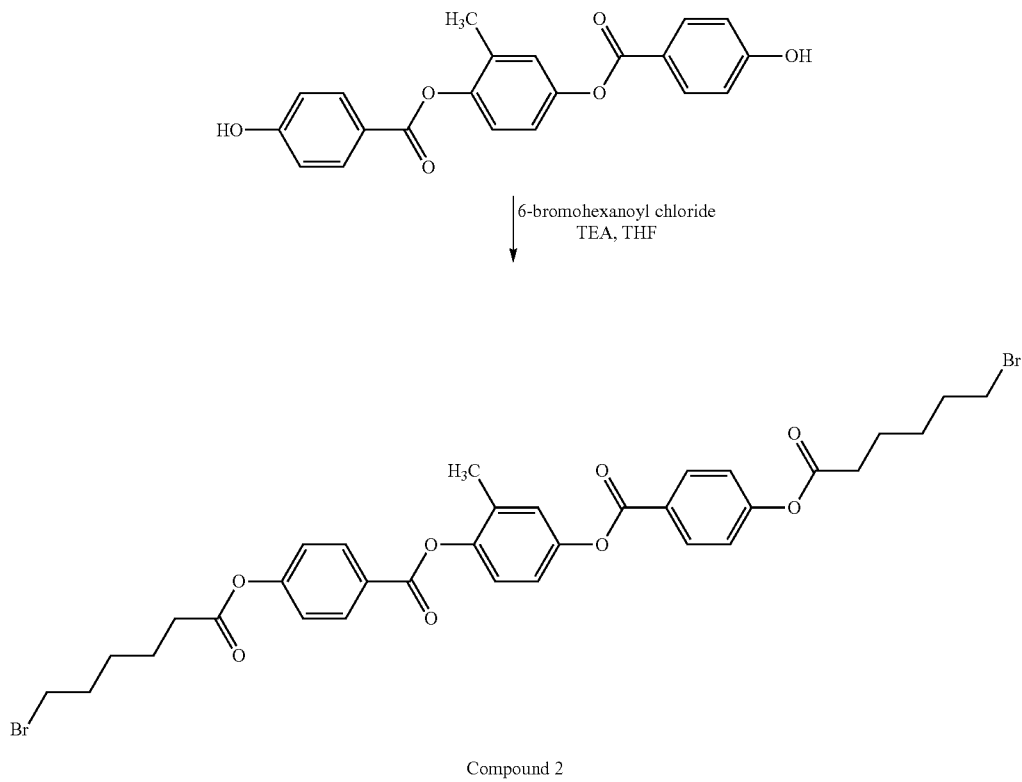

A mixture of Compound 1 (100 g), THF (750 mL), and TEA (165 mL) was cooled to 0° C. A mixture of 6-bromohexanoyl chloride (126.0 g) in THF (400 mL) was added over about 0.75 h. The mixture was stirred at 0° C. for 2 h and allowed to warm to RT, and stirred for 2 h. The mixture was poured into 1.5 L water and hydrochloric acid (37%) was added until the mixture was pH 6. The mixture was stirred for 15 min and the solids collected. The solids were rinsed with water, methanol and then dried to provide Compound 2. $^1$H NMR (CDCl$_3$, 500 MHz) δ 1.60 (m, 4H), 1.81 (m, 4H), 1.95 (m, 4H), 2.25 (s, 3H), 2.62 (t, J=7.4 Hz, 2H), 2.63 (t, J=7.4 Hz, 2H), 3.45 (t, J=6.8 Hz, 4H), 7.10 (dd, J=8.6, 2.7 Hz, 1H), 7.14 (d, J=2.7, 1H), 7.19 (d, J=8.6 Hz, 1H), 7.24 (d, J=8.7 Hz, 2H), 7.25 (d, J=8.7 Hz, 2H), 8.22 (d, J=8.7 Hz, 2H), 8.25 (d, J=8.7 Hz, 2H).

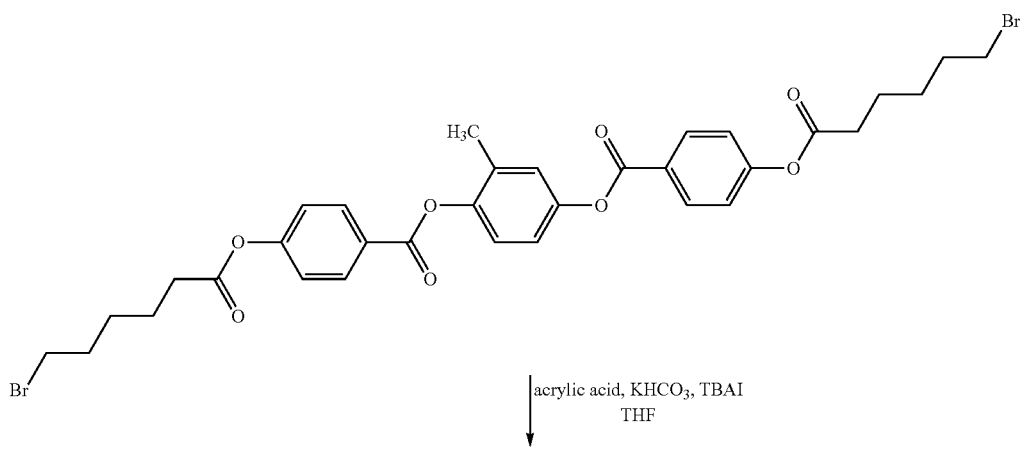

-continued

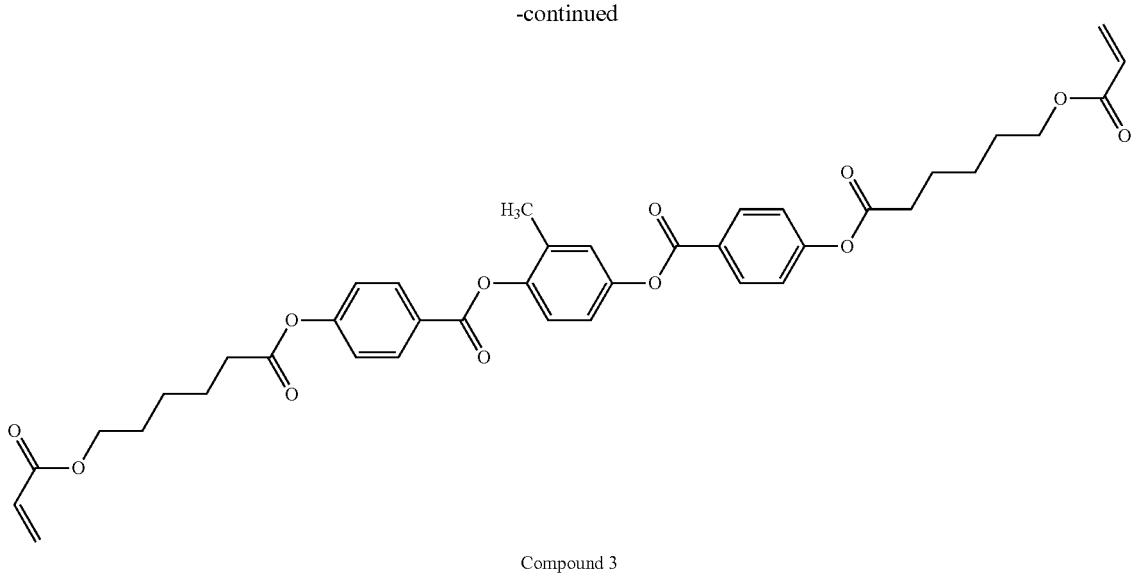

Compound 3

To a mixture of Compound 2 (20.0 g), 25.1 g potassium bicarbonate, 5.14 g tetrabutyl ammonium iodide, 1.04 g 2,6-di-tert-butyl-4-methylphenol, and THF (350 mL) was added 5.73 mL acrylic acid. The mixture was heated at 65° C. for 9 h and then allowed to stir at RT overnight. The mixture was partition between ether/water, and the ether layer washed with several portions of water. The ether layer was dried and the solvent removed and the product recrystallized from isopropanol to provide Compound 3 (17.25 g, 88%). $^1$H NMR (CDCl$_3$, 500 MHz) δ 1.54 (m=4H), 1.77 (m, 4H), 1.83 (m, 4H), 2.25 (s, 3H), 2.624 (t, J=7.4 Hz, 2H), 2.629 (t, J=7.4 Hz, 2H), 4.21 (t, J=6.6, 4H), 5.82 (dd, J=10.4, 1.3 Hz, 2H), 6.13 (dd, J=17.3, 10.4 Hz, 2H), 6.40 (dd, J=17.3, 1.3 Hz, 2H), 7.10 (dd, J=8.7, 2.7 Hz, 1H), 7.15 (d, J=2.7, 1H), 7.19 (d, J=8.7, 1H), 7.24 (d, J=8.6 Hz, 2H), 7.25 (d, J=8.6 Hz, 2H), 8.22 (D, 8.6 Hz, 2H), 8.25 (D, J=8.6 Hz, 2H).

Compound 4 was made using a similar procedure to that described above.

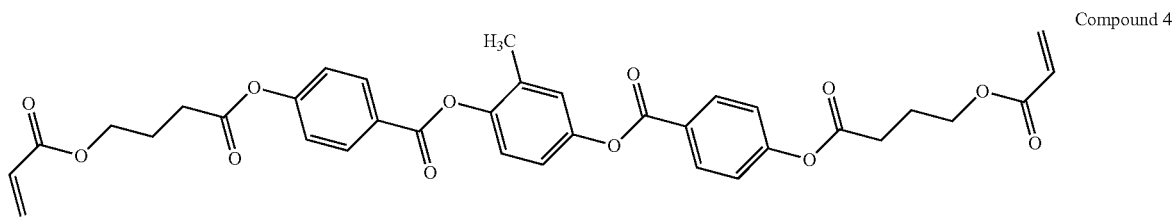

Compound 4

$^1$H NMR (CDCl$_3$, 500 MHz) δ 2.17 (m, 4H), 2.26 (s, 3H), 2.73 (t, J=7.3 Hz, 2H), 2.74 (t, J=7.3 Hz, 2H), 4.308 (t, J=6.2 Hz, 2H), 4.310 (t, J=6.2 Hz, 2H), 5.858 (dd, J=10.5, 1.4 Hz, 1H), 5.860 (dd, J=10.5, 1.4 Hz, 1H), 6.144 (dd, J=17.4, 10.5 Hz, 1H), 6.146 (dd, J=17.4, 10.5 Hz, 1H), 6.434 (dd, J=17.4, 1.4 Hz, 1H), 6.437 (dd, J=17.4, 1.4 Hz, 1H), 7.10 (dd, J=8.6, 2.8 Hz, 1H), 7.15 (d, J=2.6, 1H), 7.19 (d, J=8.8 Hz, 1H), 7.25 (d, J=8.8 Hz, 2H), 7.27 (d, J=8.8 Hz, 2H), 8.23 (d, J=8.8 Hz, 2H), 8.26 (d, J=8.8 Hz, 2H).

Compound 7, a liquid crystal monomer is made in the following manner:

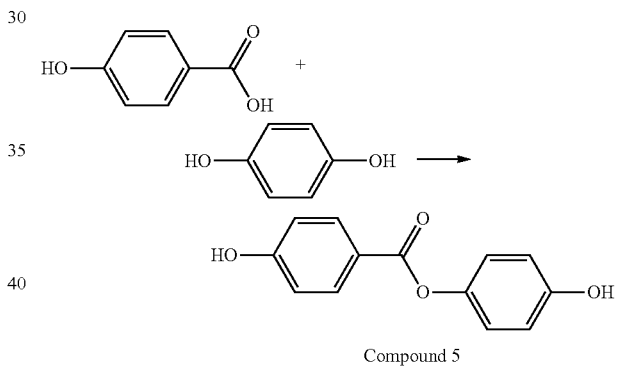

Compound 5

A mixture of 4-hydroxybenzoic acid (80 g), hydroquinone (64 g), p-toluenesulfonic acid (2 g), xylenes (500 mL) was heated to reflux in a flask equipped with a Dean-Stark trap, condenser and mechanical stirrer until about 10 mL of water were collected. After cooling to room temperature the solids were filtered off, washed with hexanes, and dried. The obtained solids were placed into 600 mL of boiling acetone and stirred for 30 min The mixture was filtered hot to eliminate traces of insoluble material. After cooling to room temperature the acetone solution was yellow but transparent.

1500 mL of DI water were added slowly to precipitate the product. The precipitated product was filtered off and dried to provide Compound 5. $^1$H NMR (CDCl$_3$, 500 MHz) δ 6.78 (d, J=8.9 Hz, 2H), 6.90 (d, J=8.8 Hz, 2H), 7.00 (d, J=8.9 Hz, 2H), 7.94 (d, J=8.8 Hz, 2H), 9.42 (s, 1H), 10.44 (s, 1H).

Example 1

This example illustrates the formation of Compound 10, a chiral monomer of one embodiment of the invention.

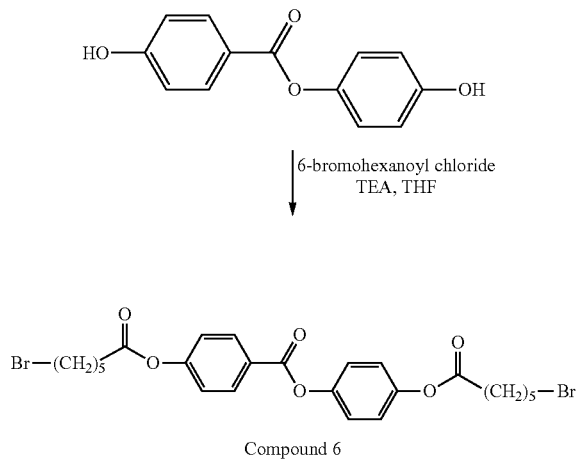

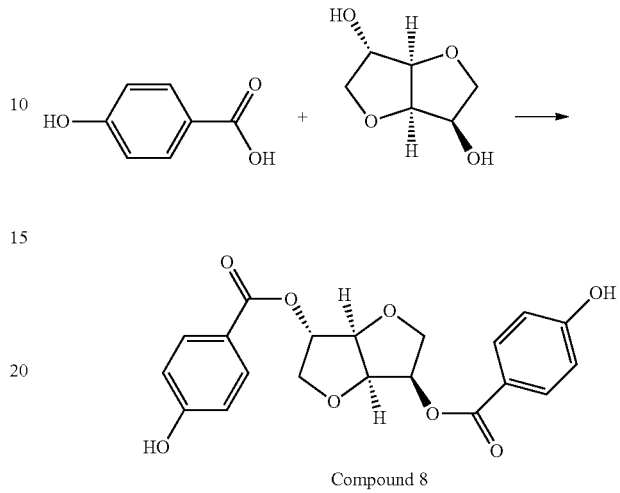

Compound 8

Compound 6 was prepared using an analogous procedure as was described above for the synthesis of Compound 2. $^1$H NMR (CDCl$_3$, 500 MHz) δ 1.59 (m, 4H), 1.80 (m, 4H), 1.94 (m, 4H), 2.59 (t, J=7.4 Hz, 2H), 2.63 (t, J=7.4 Jz, 2H), 3.441 (t, J=6.7 Hz, 2H), 3.446 (t, J=6.7 Hz, 2H), 7.14 (d, J=9.0 Hz, 2H), 7.22 (d, 9.0 Hz, 2H), 7.24 (d, 8.8 Hz, 2H), 8.22 (d, 8.8 Hz, 2H).

4-Hydroxybenzoic acid (80 g), isosorbide (40 g), p-toluenesulfonic acid (2 g), and xylenes (500 mL) were combined in a flask equipped with a Dean-Stark trap, condenser and mechanical stirrer. The reaction mixture was heated to reflux for 7 hrs at which time an additional charge of p-toluenesulfonic acid (1.0 g) was added and the mixture heated back to reflux. After 2.5 hrs, the reaction was allowed to cool to room temperature. The xylenes were decanted and the solids were taken up in 500 mL ethyl acetate, and washed with a 1% (w/v) sodium bicarbonate solution. The solvent was removed under reduced pressure, providing Compound 8. $^1$H NMR (DMSO-d$_6$, 400 MHz) δ 3.88-3.98 (m, 4H), 4.58 (d, J=4.9 Hz, 1H), 4.93 (t, J=5.3 Hz, 1H), 5.27 (br s, 1H), 5.32 (q, J=4.5 Hz, 1H), 6.85 (d, J=8.8 Hz, 2H), 6.87 (d, J=8.8 Hz, 2H), 7.81 (d, J=8.8 Hz, 2H), 7.84 (d, J=8.8 Hz, 2H), 10.36 (s, 2H).

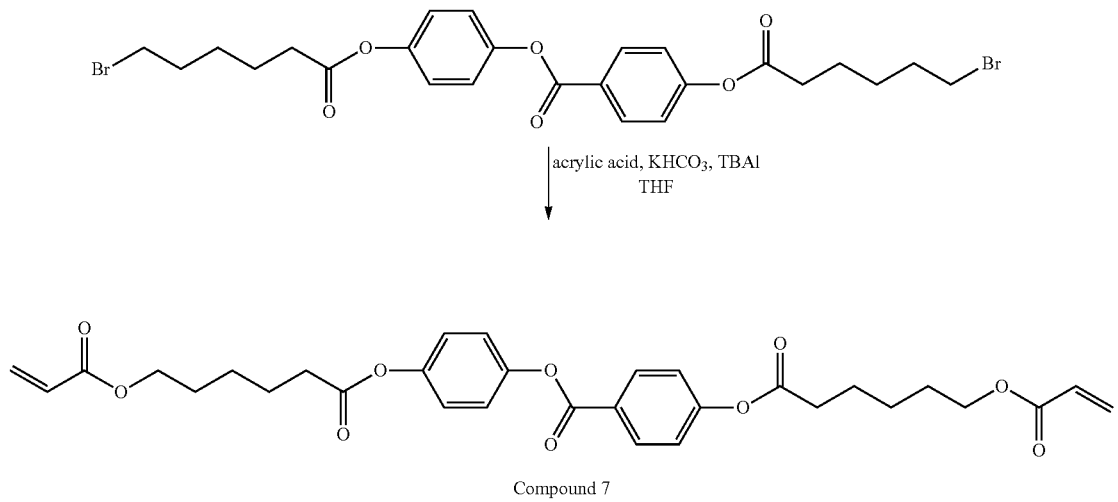

Compound 7

Compound 7 was preparing using an analogous procedure as was described above for the synthesis of Compound 3. $^1$H NMR (CDCl$_3$, 500 MHz) δ 1.52 (m, 4H), 1.76 (m, 4H), 1.78 (m, 4H), 2.59 (t, J=7.4 Hz, 2H), 2.62 (t, J=7.4 Hz, 2H), 4.19 (t, J=6.6 Hz, 2H), 4.20 (t, J=6.6 Hz, 2H), 5.823 (dd, 1H), 5.826 (dd, 1H), 6.122 (dd, 1H), 6.127 (dd, 1H), 6.404 (dd, 1H), 6.407 (dd, 1H), 7.13 (d, J=8.6 Hz, 2H), 7.21 (d, J=8.6 Hz, 2H), 7.23 (d, J=8.6 Hz, 2H), 8.21 (d, J=8.6 Hz, 2H).

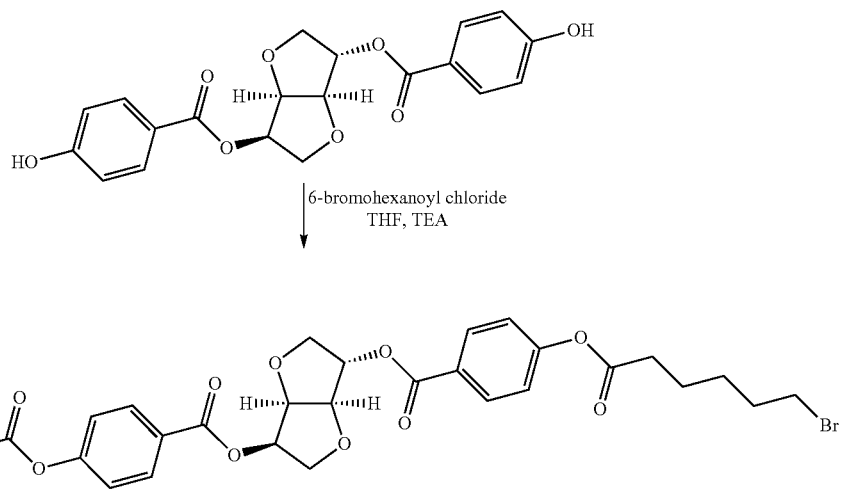

Compound 9

A mixture of Compound 8 (30 g), THF (200 mL), and triethylamine (48 mL) was cooled to 0° C. A mixture of 6-bromohexanoyl chloride (36.5 g) and tetrahydrofuran (150 mL) was added dropwise over 25 minutes. After stirring for 2 hrs the reaction was partitioned between water and diethyl ether and the organics were washed with dilute HCl, water, dried, filtered, and concentrated. The crude mixture was crystallized from isopropyl alcohol to provide Compound 9. $^1$H NMR (CDCl$_3$, 500 MHz) δ 1.59 (m, 4H), 1.80 (m, 4H), 1.93 (m, 4H), 2.60 (t, J=7.4 Hz, 2H), 2.61 (t, J=7.4 Hz, 2H), 3.43 (t, J=6.7 Hz, 2H), 3.44 (t, J=6.7, 2H), 4.07 (m, 4H), 4.66 (app d, 1H), 5.04 (app t, 1H), 5.41 (app q, 1H), 5.48 (app d, 1H), 7.16 (d, J=8.9 Hz, 2H), 7.18 (d, J=8.9 Hz, 2H), 8.04 (d, J=8.9 Hz, 2H), 8.11 (d, J=8.8 Hz, 2H).

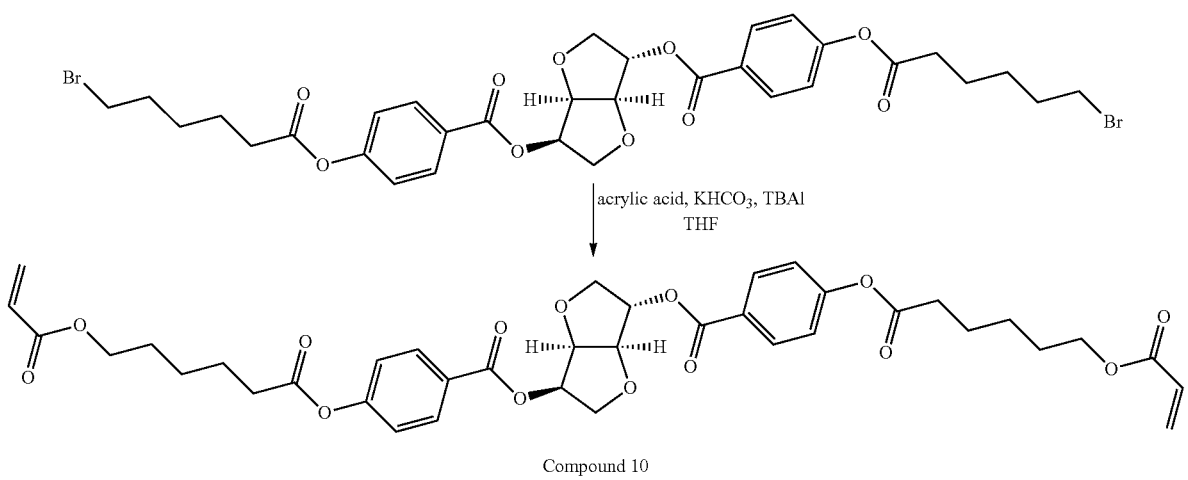

Compound 10

To a mixture of Compound 9 (40 g), potassium bicarbonate (48.7 g), tetrabutylammonium iodide (8.0 g), 2,6-di-tert-butyl-4-methylphenol (1.74 g), and THF (500 mL), was added acrylic acid (11.2 g). The mixture was heated to reflux for 6.5 hrs and stirred at RT for 16 h. The mixture was diluted with ethyl ether and washed with water. The organics were dried, filtered, concentrated, and then taken up in hot isopropyl alcohol. On cooling solids precipitated and were filtered to provide Compound 10. Melting point=50° C. $^1$H NMR (CDCl$_3$, 400 MHz) δ 1.52 (m, 4H), 1.75 (m, 4H), 1.81 (m, 4H), 2.60 (t, J=7.4 Hz, 2H), 2.61 (t, J=7.4 Hz, 2H), 4.07 (m, 4H), 4.191 (t, J=6.5 Hz, 2H), 4.194 (t, J=6.5 Hz, 2H), 4.66 (app d, J=4.7 Hz, 1H), 5.05 (app t, J=5.2 Hz, 1H), 5.41 (app q, J=5.2 Hz, 1H), 5.48 (br s, 1H), 5.82 (br d, J=10.4 Hz, 2H), 6.12 (app dd, J=17.3, 10.4 Hz, 2H), 6.40 (app d, J=17.3 Jz, 2H), 7.16 (d, J=8.4, 2H), 7.18 (d, J=8.4 Hz, 2H), 8.04 (d, J=8.8 Hz, 2H), 8.10 (d, J=8.8 Hz, 2H).

Example 2

This example illustrates the formation of Compound 13, a chiral monomer of one embodiment of the invention.

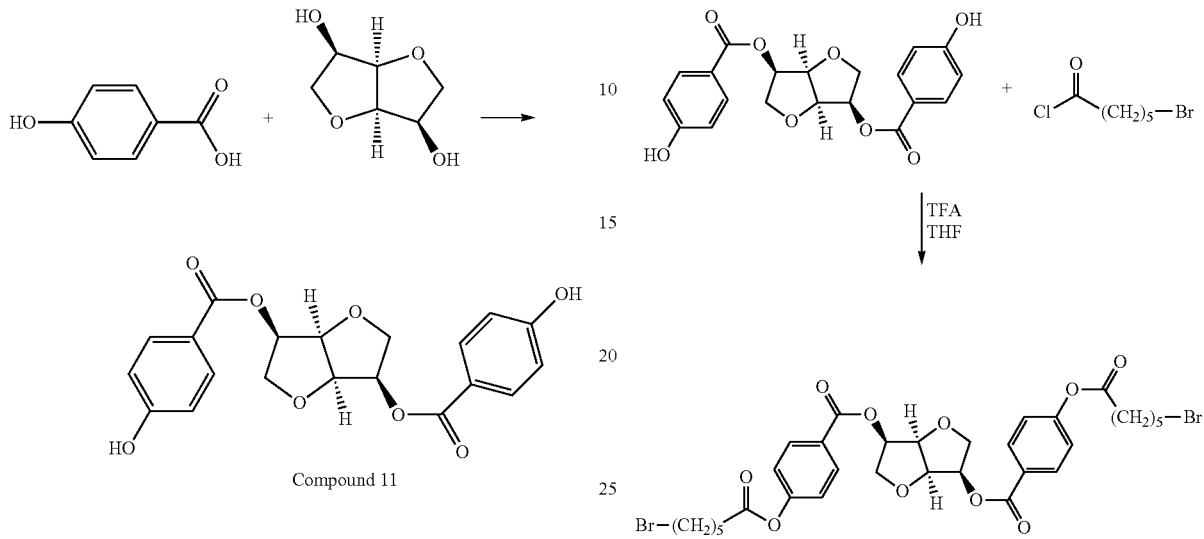

A mixture of 4-hydroxybenzoic acid (40 g), isomannide (20 g), toluene (85 mL), diethylene glycol dimethyl ether (4 mL), and concentrated sulfuric acid (1 g) was heated to reflux for 8 h under nitrogen. After cooling to RT, ethyl acetate (200 mL) was added and the mixture stirred for 2 h at 60° C. The mixture was cooled to RT and the resulting solid filtered and dried to provide Compound 11. $^1$H-NMR (DMSO-d$_6$, 500 MHz): δ 3.85 (d of d, 2H, J$_{HH}$=9.3 Hz); 4.05 (d of d, 2H, J$_{HH}$=9.3 Hz); 4.78 (m, 2H); 5.23 (m, 2H); 6.89 (d, 4H); 7.87 (d, 4H); 10.35 (s, 2H).

Compound 12 was prepared using an analogous procedure as was described above for the synthesis of Compound 9. $^1$H NMR (DMSO-d$_6$, 500 MHz): δ 1.50 (m, 4H); 1.69 (m, 4H); 1.86 (m, 4H); 2.64 (t, 4H, J$_{HH}$=7.2 Hz); 3.56 (t, 4H, J$_{HH}$=6.6 Hz); 3.90 (d of d, 2H, J$_{HH}$=9.1 Hz); 4.07 (d of d, 2H, J$_{HH}$=9.2 Hz); 4.82 (m, 2H); 5.29 (m, 2H); 7.31 (m, 4H); 8.06 (m, 4H).

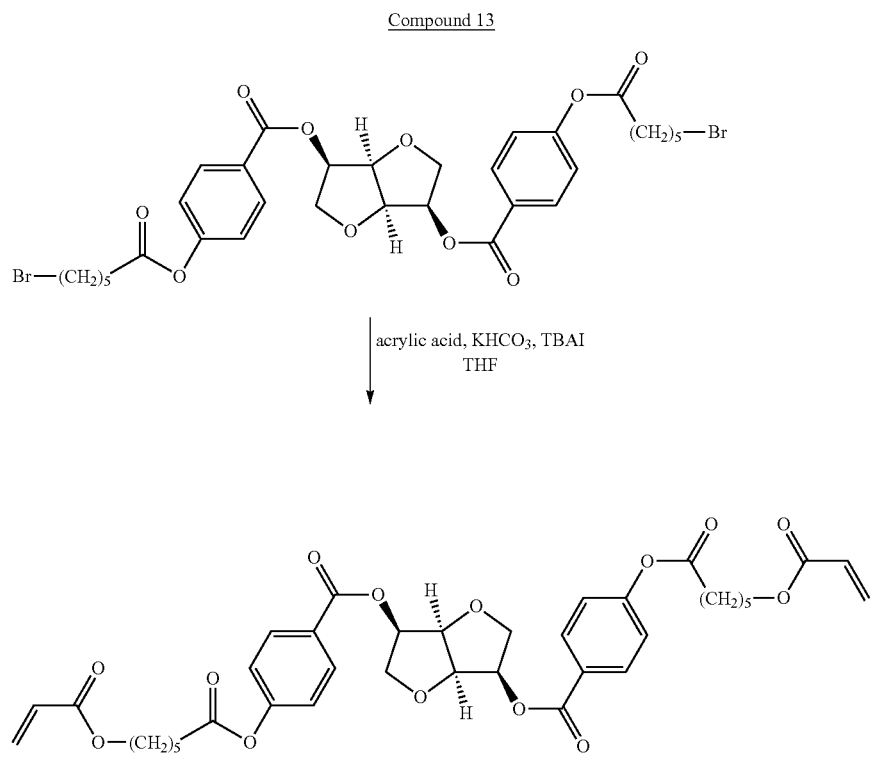

Compound 13 was prepared using an analogous procedure as was described above for the synthesis of Compound 10. Melting point=49° C. $^1$H NMR (CDCl$_3$, 500 MHz) δ 1.52 (m, 4H), 1.75 (m, 4H), 1.81 (m, 4H), 2.60 (t, J=7.4 Hz, 4H), 3.99 (dd, J=9.4, 6.5 Hz, 2H), 4.13 (dd, J=9.4, 6.5 Hz, 2H), 4.20 (t, J=6.6 Hz, 4H), 4.87 (dd, J=4.1, 1.3 Hz, 2H), 5.33 (m, 2H), 5.82 (dd, J=10.5, 1.4 Hz, 2H), 6.12 (dd, J=17.3, 10.4 Hz, 2H), 6.40 (dd, J=17.3, 1.4 Hz, 2H), 7.18 (d, J=8.7 Hz, 4H), 8.12 (d, 8.7 Hz, 4H).

Example 3

This example illustrates the formation of Compound 16, a chiral monomer of one embodiment of the invention.

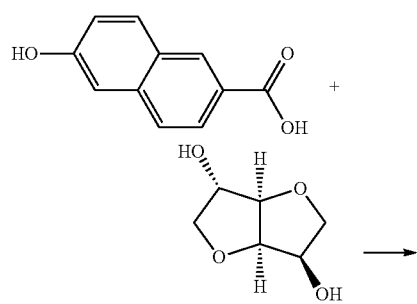

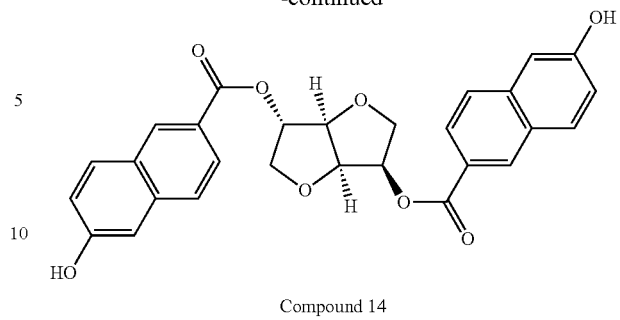

Compound 14

6-Hydroxy-naphthalene-2-carboxylic acid (56 g), isosorbide (20 g), p-toluenesulfonic acid (1 g), and xylenes (250 mL) were combined in a flask equipped with a Dean-Stark trap, condenser and mechanical stirrer. The reaction mixture was heated to reflux until 5 mL of water were collected in the trap (~24 hrs). During this time two additional charges of p-toluenesulfonic acid (1.0 g) were added. After cooling to room temperature the xylenes were decanted and the solids were rinsed with hexanes. The material was purified by dissolving it in 200 mL of acetone and precipitating the solution into 1 L of 1% aqueous sodium bicarbonate solution. Compound 14 was obtained as a yellowish solid. $^1$H NMR (DMSO-d$_6$, 500 MHz) δ 4.05-4.10 (m, 4H), 4.71 (d, J=4.9 Hz, 1H), 5.08 (t, J=5.3 Hz, 1H), 5.43 (br m, 1H), 5.46 (q, J=4.5 Hz, 1H), 7.20-7.25 (m, 4H), 7.77-8.04 (m, 6H), 8.52 (d, J=20.1 Hz, 2H), 10.44 (s, 2H).

Compound 15

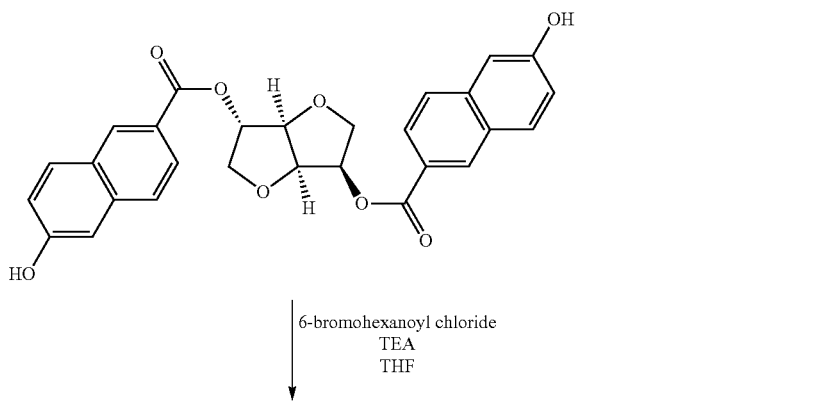

| 6-bromohexanoyl chloride
TEA
THF

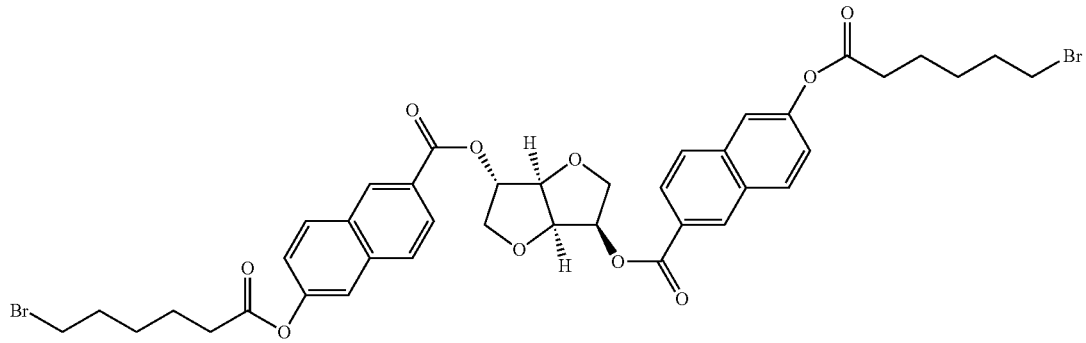

A mixture of Compound 14 (20 g), THF (200 mL), and TEA (25 mL) was cooled to 0° C. A mixture of 6-bromohexanoyl chloride (19 g) and THF (50 mL) was added dropwise maintaining the reaction temperature below 5° C. After the addition the reaction mixture was allowed to warm up to room temperature were it remained stirring overnight. The precipitated salts formed during the reaction were filtered off and rinsed with 50 mL of THF. The filtered solution was poured into 600 mL of deionized water and stirred for two hors at room temperature. The precipitated product was filtered, washed with water, and dried under vacuum at 60° C. overnight. Compound 15 was obtained as a light yellow solid. $^1$H NMR (DMSO-d$_6$, 500 MHz) δ 1.53 (m, 4H), 1.72 (m, 4H), 1.88 (m, 4H), 2.66 (t, J=7.3 Hz, 2H), 2.68 (t, J=7.3 Hz, 2H), 3.56 (t, J=6.7 Hz, 2H), 3.57 (t, J=6.7, 2H), 4.04-4.12 (m, 4H), 4.74 (d, J=4.9 Hz, 1H), 5.11 (t, J=5.3 Hz, 1H), 5.46 (app t, 1H), 5.50 (app q, 1H), 7.41-7.46 (m, 2H), 7.79 (d of d, 2H), 7.99-8.08 (m, 4H), 8.23 (d of d, 2H), 8.69 (d, J=22 Hz, 2H).

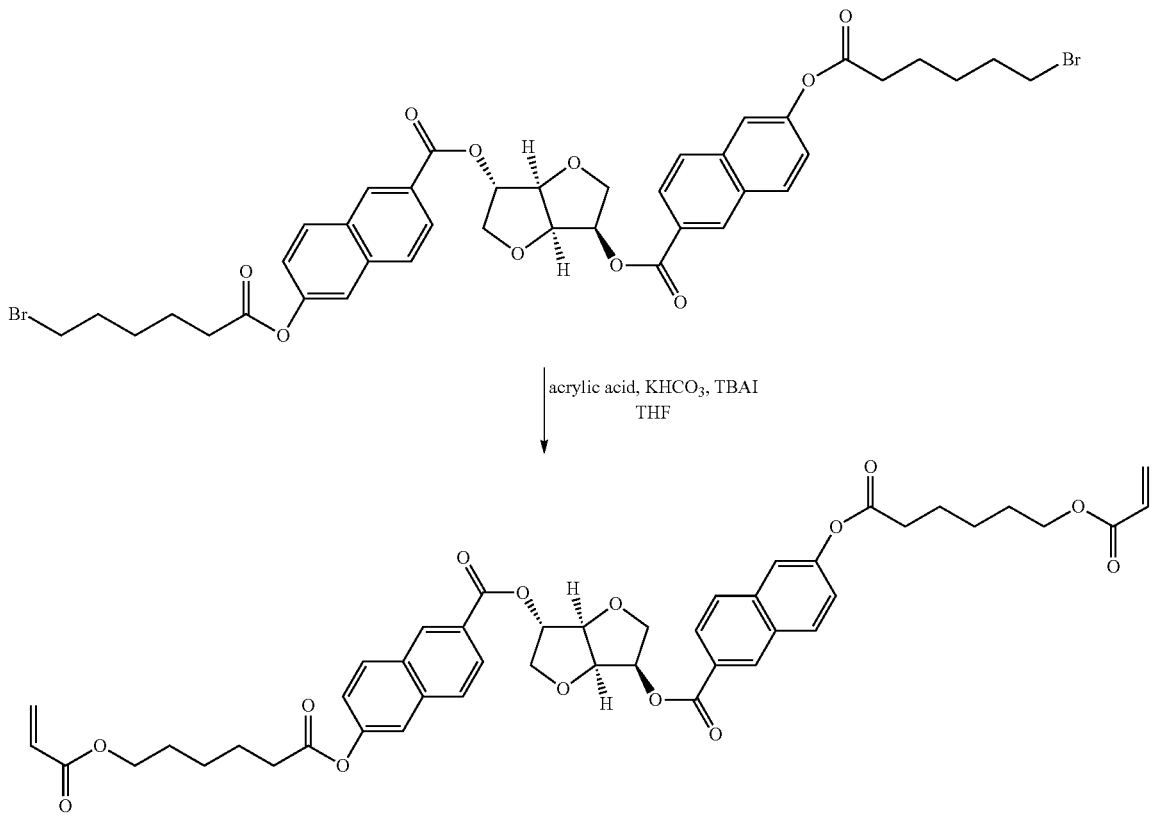

Compound 16

To a mixture of Compound 15 (20 g), potassium bicarbonate (20 g), tetrabutylammonium iodide (3.5 g), 2,6-di-tert-butyl-4-methylphenol (1 g), and THF (200 mL), was added acrylic acid (5.3 g). The mixture was heated to reflux for seven hours and stirred at room temperature overnight. The reaction mixture was poured into 300 mL of deionized water, acidified with HCl until pH-6, and stirred for 30 minutes at room temperature. The solids were filtered off and dried under vacuum at room temperature. The product was further purified by dissolving it in 150 mL of methanol at room temperature, filtering off insoluble material, and pouring the solution into water to precipitate the product. After filtering and drying, Compound 16 was obtained as a light yellow powder. Melting point=106-108° C. $^1$H NMR (DMSO-d$_6$, 500 MHz) δ 1.48 (m, 4H), 1.72 (m, 8H), 2.67 (t, J=7.3 Hz, 2H), 2.68 (t, J=7.3 Hz, 2H), 4.05-4.17 (m, 8H), 4.75 (app d, J=4.9 Hz, 1H), 5.11 (app t, J=5.3 Hz, 1H), 5.47 (br t, 1H), 5.50 (app q, J=5.3 Hz, 1H), 5.93 (d of t, J=10.3 Hz, 2H), 6.19 (app dd, J=17.3, 10.4 Hz, 2H), 6.34 (d of t, J=17.3 Jz, 2H), 7.41-7.45 (m, 2H), 7.79 (d of d, J=7.2, 2.1 Hz, 2H), 7.99-8.08 (m, 4H), 8.22 (d of d, J=20.1, 8.9 Hz, 2H), 8.69 (d, J=21.5 Hz, 2H).

Example 4

This example illustrates the formation of Compound 19, a chiral monomer of one embodiment of the invention.

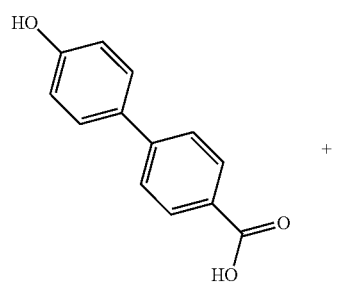

+

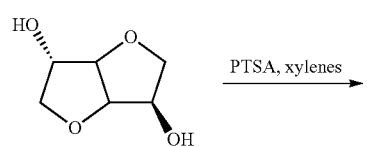

→ PTSA, xylenes →

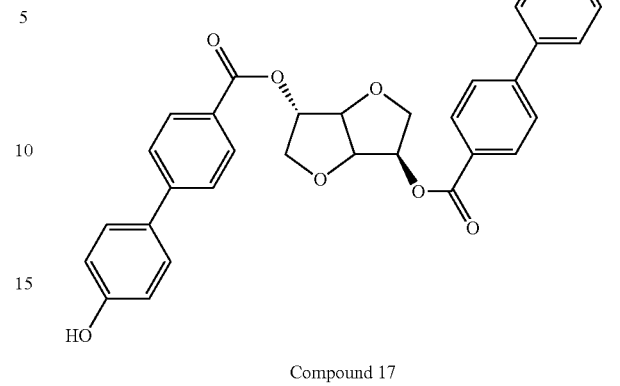

Compound 17

To a three neck round-bottom flask equipped with Dean-Stark Trap, mechanic stir, and nitrogen flow adapter, isosorbide (3.4 g), 4'-hydroxybiphenyl-4-carboxylic acid (5.0 g), p-toluenesulphonic acid monohydrate (0.2 g), and xylenes (60 mL) were charged and heated to reflux for 20 h. The reaction mixture was then cooled down to room temperature. The crude mixture was collected by filtration and was then resuspended in acetone, filtered, and washed further with acetone to obtain Compound 17. $^1$H NMR (DMSO-d$_6$, 500 MHz) δ 4.02 (m, 4H), 4.66 (d, J=5.0 Hz, 1H), 5.01 (t, J=5.3 Hz, 1H), 5.37 (br s, 1H), 5.41 (q, J=5.0 Hz, 1H), 6.89 (m, 4H), 7.59 (m, 4H), 7.76 (m, 4H), 8.00 (m, 4H).

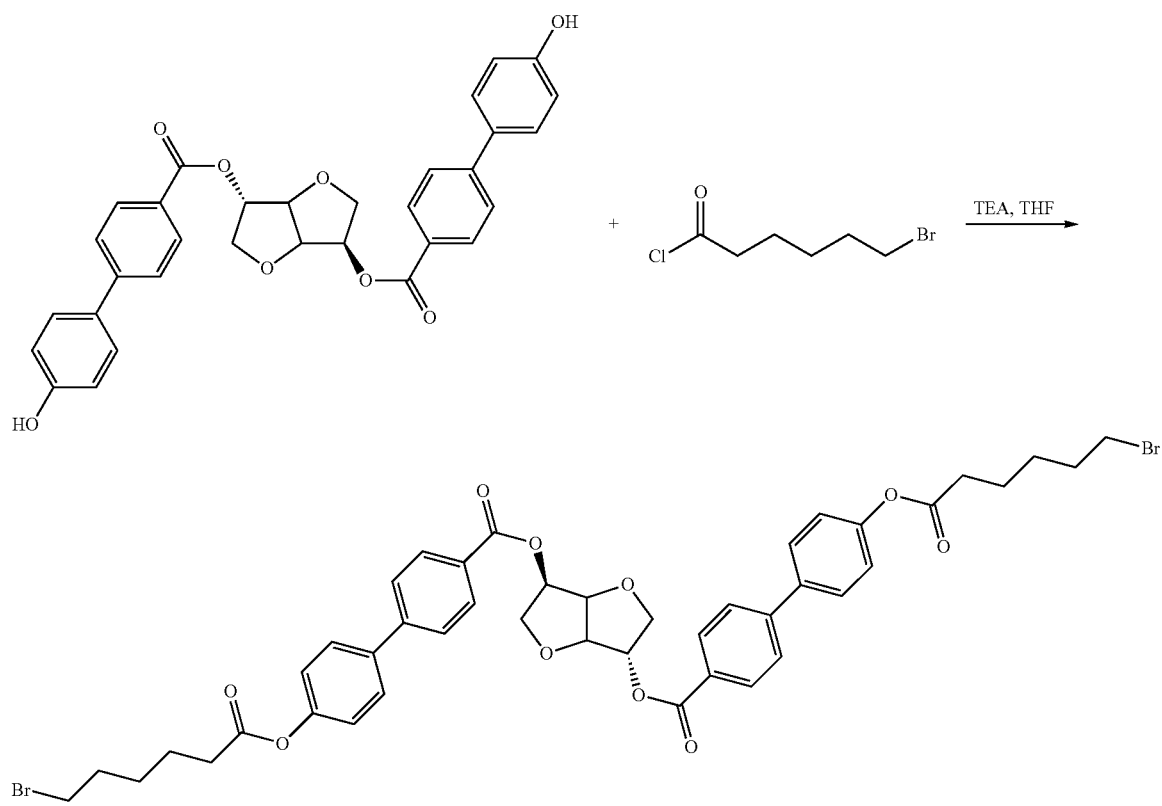

Compound 18

Compound 18 was prepared using a similar procedure as was described above for the synthesis of Compound 9. ¹H NMR (CDCl₃, 500 MHz) δ 1.60 (m, 4H), 1.81 (m, 4H), 1.94 (m, 4H), 2.61 (t, J=7.5 Hz, 2H), 2.62 (t, J=7.5 Hz, 2H), 3.44 (app t, J=6.5 Hz, 4H), 4.05-4.20 (m, 4H), 4.72 (app d, J=4.7 Hz, 1H), 5.09 (app t, J=5.1 Hz, 1H), 5.46 (app q, J=5.5 Hz, 1H), 5.52 (br s, 1H), 7.19 (m, 4H), 7.63 (m, 8H), 8.11 (m, 4H).

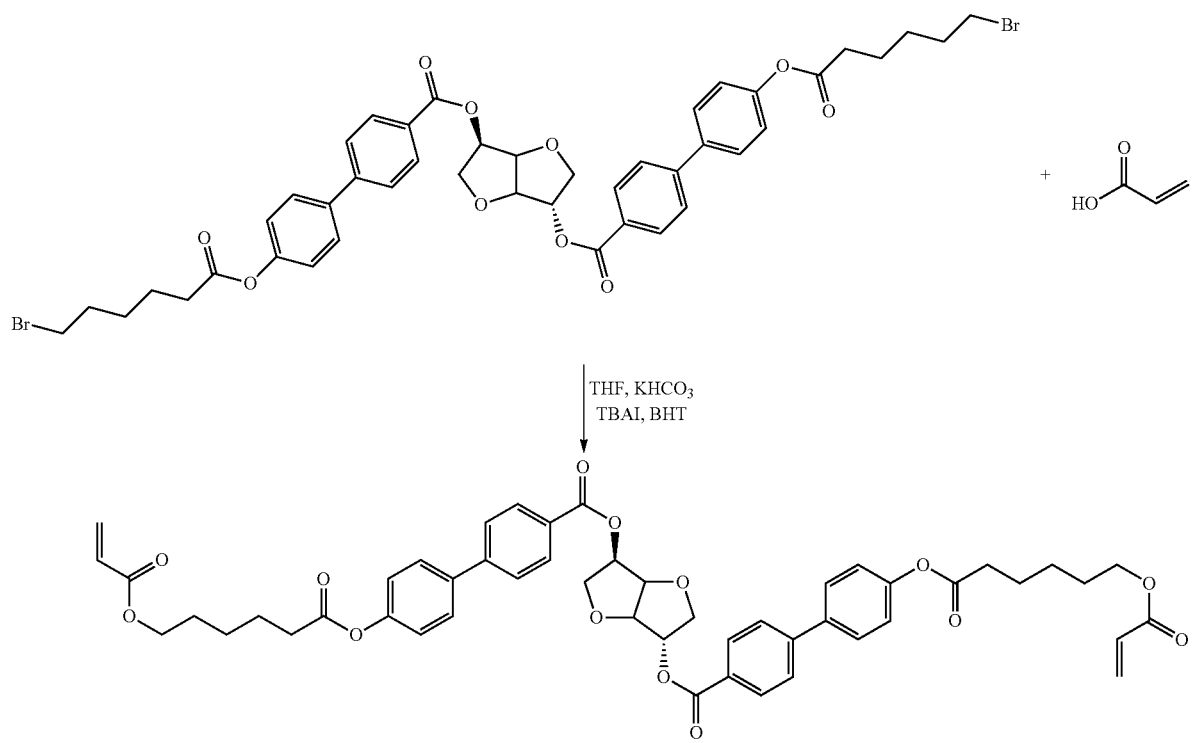

Compound 19

Compound 19 was prepared using a similar procedure as was described above for the synthesis of Compound 10. Melting point=162-163° C. ¹H NMR (CDCl₃, 400 MHz) δ 1.46 (m, 4H), 1.69 (m, 4H), 1.76 (m, 4H), 2.54 (t, J=7.0 Hz, 4H), 4.05 (m, 4H), 4.12 (t, J=6.2 Hz, 2H), 4.13 (t, J=6.6 Hz, 2H), 4.64 (app d, J=4.6 Hz, 1H), 5.02 (app t, J=5.0 Hz, 1H), 5.39 (app q, J=5.4 Hz, 1H), 5.45 (br, 1H), 5.75 (app d, J=10.4 Hz, 2H), 6.06 (app dd, J=17.3, 10.4 Hz, 2H), 6.34 (app d, J=17.3 Hz, 2H), 7.11 (m, 4H), 7.56 (m, 8H), 8.04 (m, 4H).

Example 5

This example illustrates an alternate synthetic route as applied to the synthesis of Compound 19, a chiral monomer of one embodiment of the invention.

Synthesis of 6-hydroxyhexanoic acid was preformed following the procedure reported in PCT/JP2005/004389.

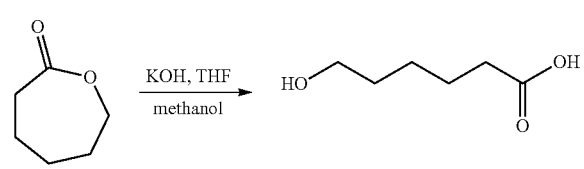

Caprolactone (100 g) was added to a mixture of potassium hydroxide (145 g), methanol (110 mL), and THF (390 mL). The resulting mixture was stirred at room temperature overnight. The solution was then acidified with HCl and extracted with ethyl acetate. The combined organic layers were washed with water, dried, filtered, and concentrated to obtain 6-hydroxyhexanoic acid. ¹H NMR (CDCl₃, 500 MHz) δ 1.44 (m, 2H), 1.60 (m, 2H), 1.68 (m, 2H), 2.37 (t, J=7.5 Hz, 2H), 3.66 (t, J=6.5 Hz, 2H), 5.80 (br, 1H).

Synthesis of 6-acryloyloxyhexanoic acid was performed following the procedure reported in PCT/JP2005/004389.

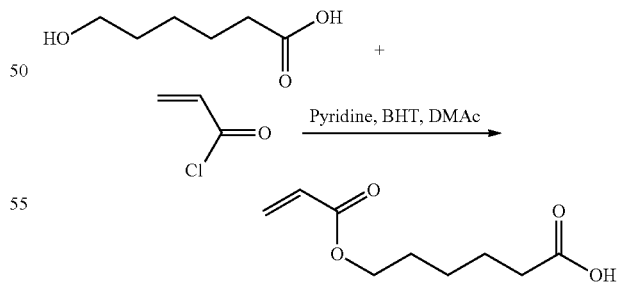

A mixture of 6-hydroxyhexanoic acid (10 g), 2,6-di-tert-butyl-4-methylphenol (0.5 g), and dimethylacetamide (57 mL) was cooled to 0° C. Acryloyl chloride (17.2 g) was then added dropwise. After stirring for 3.5 hrs, pyridine (12 mL) and water (12 mL) were slowly added. After stirring for another 2 hrs, the solution was acidified with dilute HCl and extracted with ethyl acetate. The combined organic layer was washed with water, dried, filtered, and concentrated to afford 6-acryloyloxyhexanoic acid. $^1$H NMR (CDCl$_3$, 500 MHz) δ 1.46 (m, 2H), 1.70 (m, 4H), 2.37 (t, J=7.3 Hz, 2H), 4.17 (t, J=6.4 Hz, 2H), 5.82 (d, J=10.4 Hz, 1H), 6.12 (dd, J=17.3, 10.5 Hz, 1H), 6.39 (d, J=17.3 Hz, 1H), 11.59 (br, 1H).

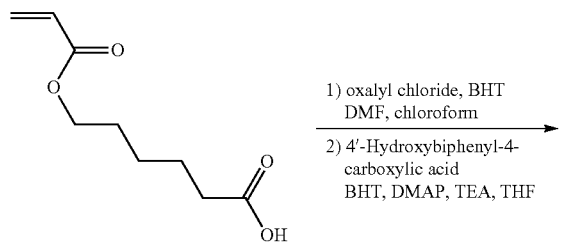

and chloroform (20 mL) were then added dropwise. After stirring for 3 hrs, the solvent was removed and the resulting acid chloride was re-dissolved in a mixture of chloroform (20 mL) and tetrahydrofuran (20 mL). The acid chloride solution was then transferred to a mixture of 4'-hydroxy-4-biphenyl-carboxylic acid (5.76 g), triethylamine (5.2 mL), 4-dimethylaminopyridine (0.13 g), 2,6-di-tert-butyl-4-methylphenol (0.3 g), and tetrahydrofuran (55 mL) which had been cooled to 0° C. After stirring for 12 hrs, the reaction mixture was added to water, acidified with dilute HCl, extracted with chloroform, dried, filtered, and concentrated. The crude mixture was purified by washing with acetonitrile and isopropanol to obtain Compound 20. $^1$H NMR (DMSO-d$_6$, 500 MHz) δ 1.45 (m, 2H), 1.69 (m, 4H), 2.63 (t, J=7.4 Hz, 2H), 4.14 (t, J=6.6 Hz, 2H), 5.94 (app d, J=10.3 Hz, 1H), 6.18 (app dd, J=17.3, 10.4 Hz, 1H), 6.33 (app d, J=17.3 Hz, 1H), 7.24 (m, 2H), 7.79 (m, 4H), 8.02 (m, 2H), 12.95 (br, 1H).

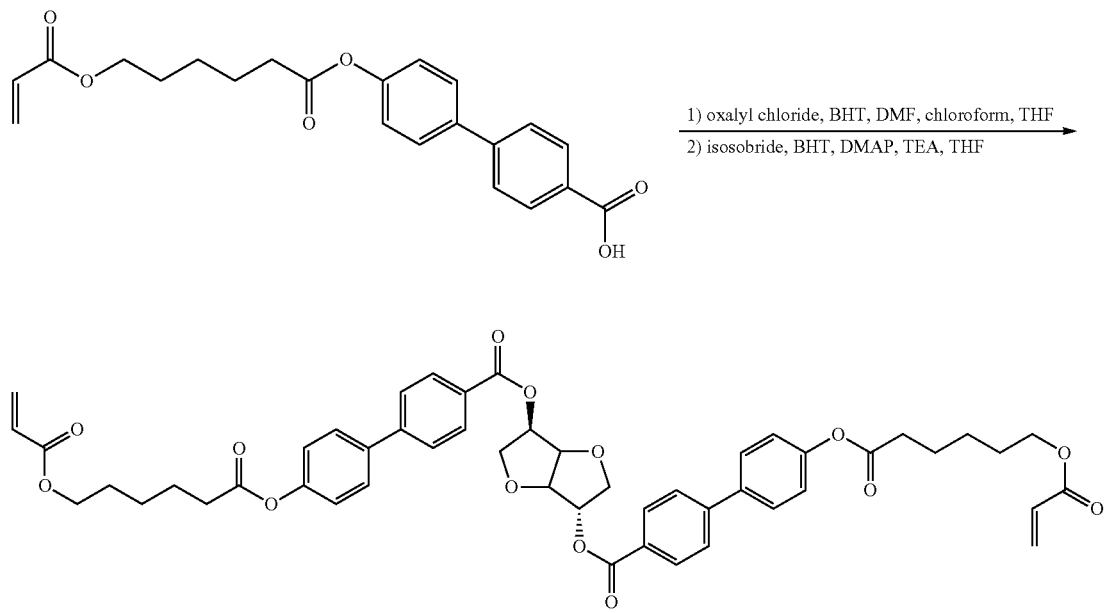

Compound 19

-continued

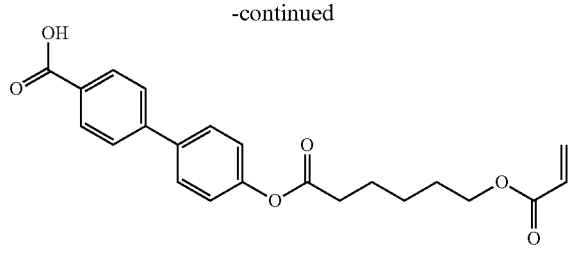

Compound 20

A mixture of 6-acryloyloxyhexanoic acid (5.0 g), 2,6-di-tert-butyl-4-methylphenol (0.3 g), chloroform (30 mL), and DMF (10 drops) was cooled to 0° C. Oxalyl chloride (5.12 g)

A mixture of Compound 20 (3.0 g), 2,6-di-tert-butyl-4-methylphenol (0.14 g), tetrahydrofuran (20 mL), and DMF (6 drops) was cooled to 0° C. Oxalyl chloride (1.49 g) and tetrahydrofuran (20 mL) were then added dropwise. After stirring for 7 hrs, the solvent was removed and the resulting acid chloride was re-dissolved in tetrahydrofuran (30 mL) and added dropwise to a mixture of isosorbide (0.26 g), triethylamine (0.77 mL), 4-dimethylaminopyridine (0.2 g), 2,6-di-tert-butyl-4-methylphenol (0.09 g), and tetrahydrofuran (15 mL) which had been cooled to 0° C. After stirring for 12 hrs, the reaction mixture was added to water, acidified with dilute HCl, extracted with chloroform, dried, filtered, and concentrated. The crude mixture was re-suspended in methanol, filtered, and washed further with methanol to obtain Compound 19.

Example 6

This example illustrates the formation of Compound 21, a chiral monomer of one embodiment of the invention.

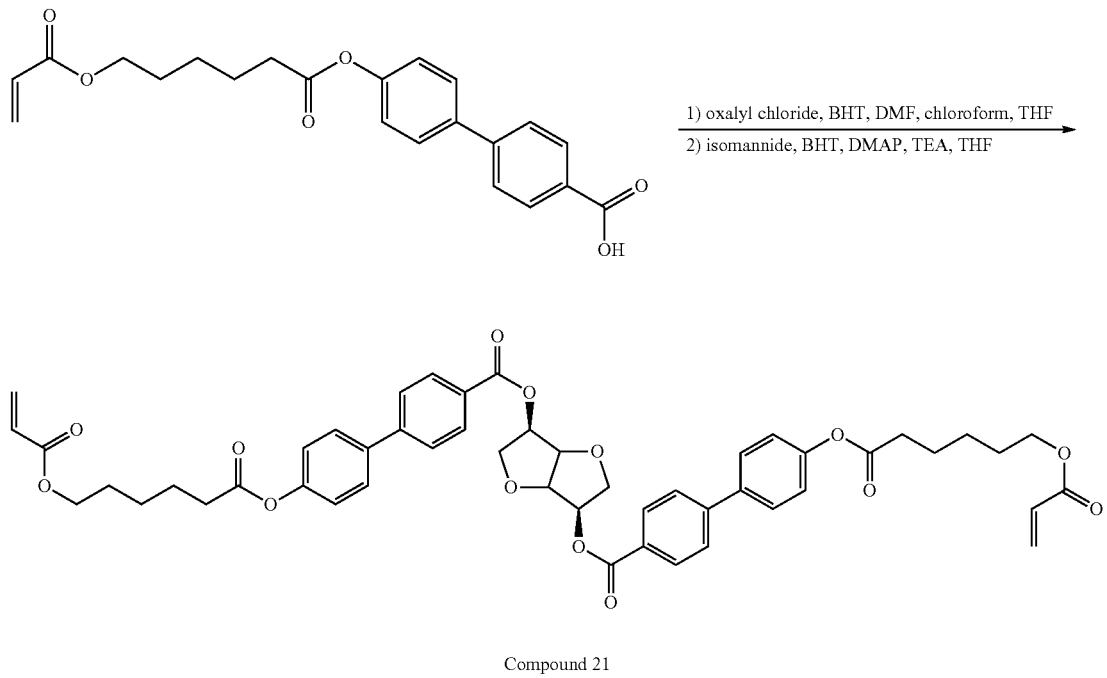

Compound 21

Compound 21 was prepared using a similar procedure to that described in Example 5 above for the synthesis of Compound 19, except isosorbide was replaced with isomannide Melting point=133-134° C. $^1$H NMR (CDCl$_3$, 400 MHz) δ 1.46 (m, 4H), 1.69 (m, 4H), 1.76 (m, 4H), 2.54 (t, J=7.4 Hz, 4H), 3.98 (m, 4H), 4.10 (t, J=6.4 Hz, 2H), 4.13 (t, J=6.6 Hz, 2H), 4.84 (br, 2H), 5.30 (br, 2H), 5.75 (app d, J=10.4 Hz, 2H), 6.06 (app dd, J=17.3, 10.4 Hz, 2H), 6.34 (app d, J=17.3 Hz, 2H), 7.11 (m, 4H), 7.56 (m, 8H), 8.09 (m, 4H).

Example 7

This example illustrates the formation of Compound 24, a chiral monomer of one embodiment of the invention.

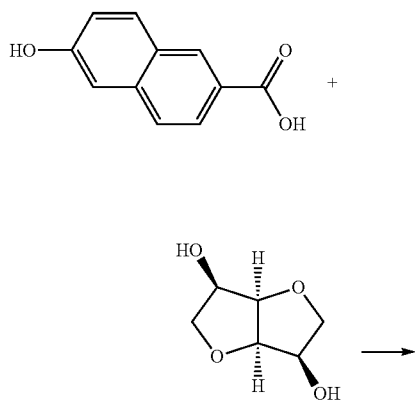

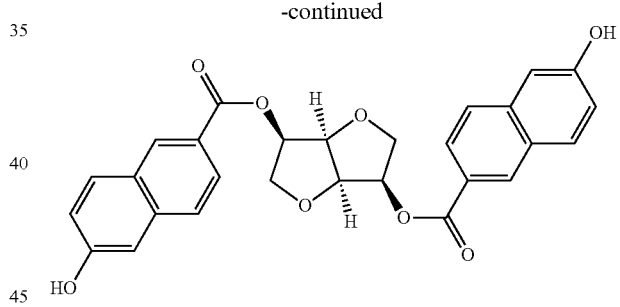

Compound 22

6-Hydroxy-naphthalene-2-carboxylic acid (56 g), isomannide (20 g), p-toluenesulfonic acid (1 g), and xylenes (250 mL) were combined in a flask equipped with a Dean-Stark trap, condenser and mechanical stirrer. The reaction mixture was heated to reflux until 5 mL of water were collected in the trap (~24 hrs). During this time two additional charges of p-toluenesulfonic acid (1.0 g) were added. After cooling to room temperature the xylenes were decanted and the solids were rinsed with hexanes. The material was purified by dissolving it in 200 mL of acetone and precipitating the solution into 1 L of 1% aqueous sodium bicarbonate solution. Compound 22 was obtained as a yellowish solid. $^1$H NMR (DMSO-d$_6$, 500 MHz) δ 4.01 (dd, J=9.2, 6.5 Hz, 2H), 4.14 (dd, J=9.3, 6.3 Hz, 2H), 4.89 (m, 2H), 5.36 (m, 2H), 7.20-7.26 (m, 4H), 7.82 (d, J=8.6 Hz, 2H), 7.95 (dd, J=8.6, 1.8 Hz, 2H), 8.01 (d, J=8.9 Hz, 2H), 8.57 (s, 2H), 10.23 (s, 2H).

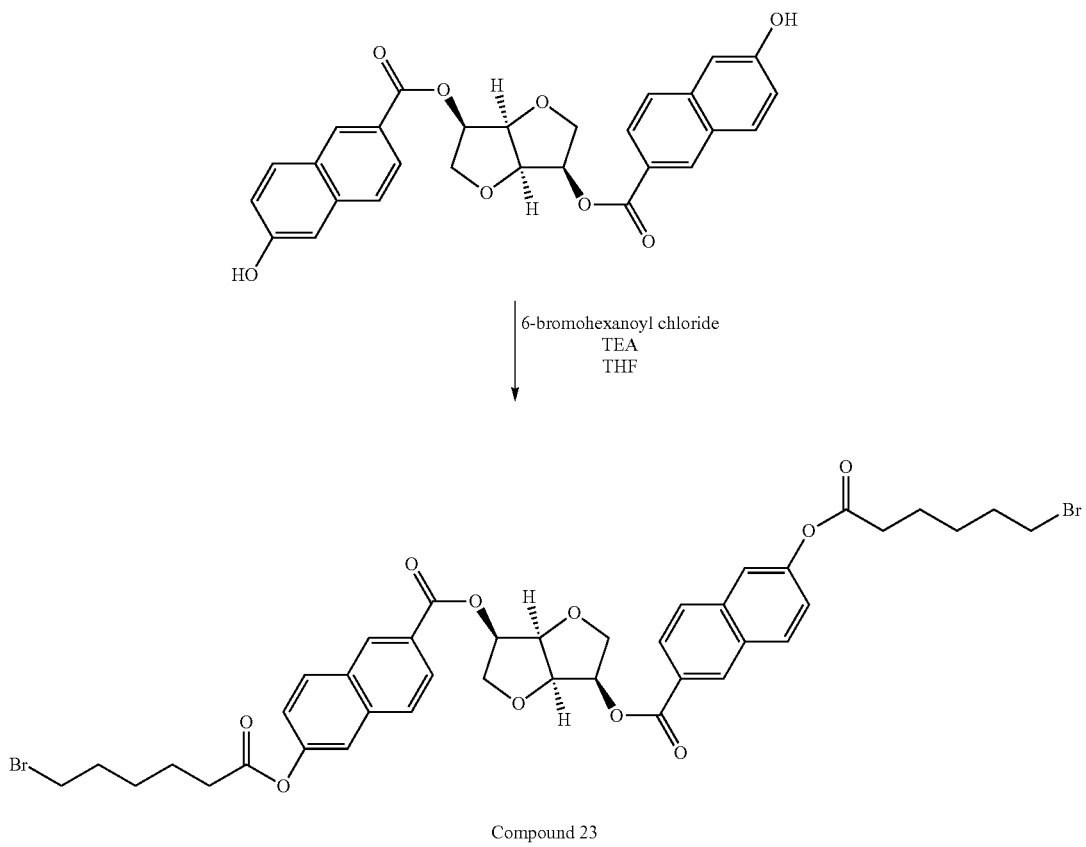

Compound 23

A mixture of Compound 22 (11 g), THF (100 mL), and triethylamine (10 mL) was cooled to 0° C. A solution of 6-bromohexanoyl chloride (11 g) in tetrahydrofuran (50 mL) was added dropwise maintaining the reaction temperature below 5° C. After the addition, the reaction mixture was allowed to warm up to room temperature were it remained stirring overnight. The precipitated salts formed during the reaction were filtered off and rinsed with 100 mL of THF. The filtered solution was poured into 1000 mL of deionized water and stirred for two hours at room temperature. The precipitated product was filtered, washed with water, and dried under vacuum at 60° C. overnight. Compound 23 was obtained as a light yellow solid. $^1$H NMR (CDCl$_3$, 500 MHz) δ: 1.54 (m, 4H), 1.75 (m, 4H), 1.87 (m, 4H), 2.57 (t, J=7.4 Hz, 4H), 3.37 (t, J=6.7 Hz, 4H), 4.03 (dd, J=9.3, 6.7 Hz, 2H), 4.11 (dd, J=9.3, 6.5 Hz, 2H), 4.87 (m, 2H), 5.33 (m, 2H), 7.22 (dd, J=8.9, 2.4 Hz, 2H), 7.54 (d, J=2.2 Hz, 2H), 7.77 (d, J=8.7 Hz, 2H), 7.90 (d, J=8.9 Hz, 2H), 8.05 (dd, J=8.6, 1.6 Hz, 2H), 8.59 (s, 2H).

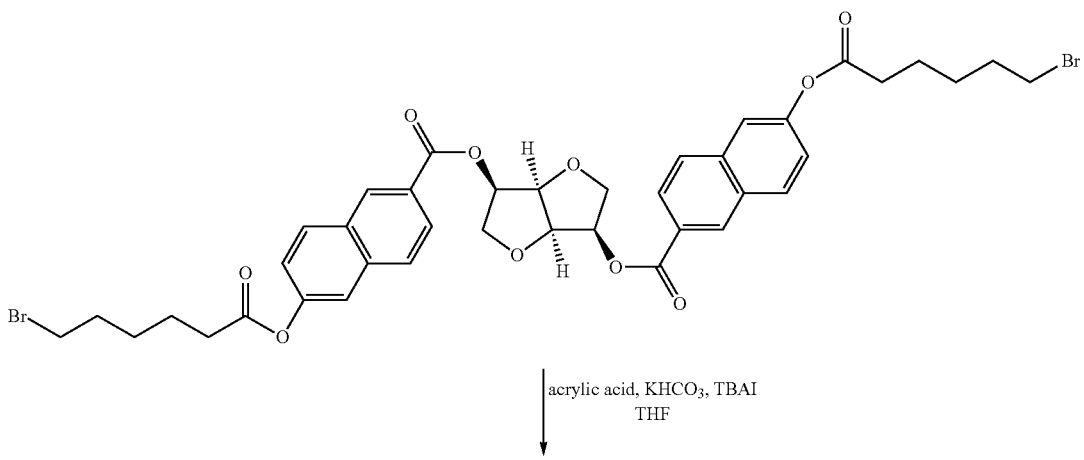

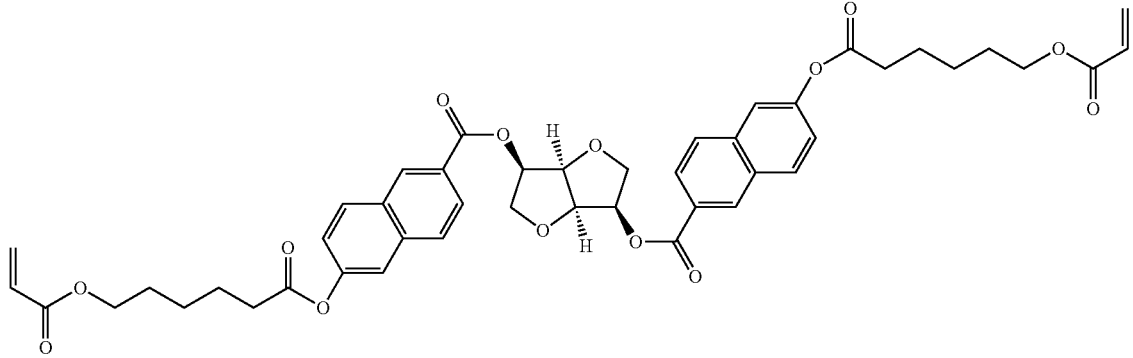

Compound 24

To a mixture of Compound 23 (14 g), potassium bicarbonate (14 g), tetrabutylammonium iodide (2.5 g), 2,6-di-tert-butyl-4-methylphenol (1 g), and THF (150 mL), was added acrylic acid (4.0 mL). The mixture was heated to reflux for seven hours and stirred at room temperature overnight. The reaction mixture was filtered and the filtrate was poured into 600 mL of deionized water and stirred for 30 minutes at room temperature. The precipitated solids were filtered off and dried under vacuum at room temperature. Compound 24 was obtained as a light yellow powder. Melting Point=146-147° C. $^1$H NMR (DMSO-$d_6$, 500 MHz) δ 1.48 (m, 4H), 1.71 (m, 8H), 2.68 (t, J=7.3 Hz, 4H), 4.03 (d of d, J=9.1, 6.3 Hz, 2H), 4.11-4.18 (m, 6H), 4.90 (m, 2H), 5.38 (m, 2H), 5.94 (dd, J=10.4, 1.5 Hz, 2H), 6.19 (dd, J=17.3, 10.4 Hz, 2H), 6.34 (dd, J=17.3, 1.5 Hz, 2H), 7.43 (dd, J=8.9, 2.2 Hz, 2H), 7.79 (d, J=2.0 Hz, 2H), 8.07 (m, 4H), 8.23 (d, J=9.0 Hz, 2H), 8.72 (s, 2H).

Example 8

This example illustrates the formation of mesogens of the general formulas IVa and IVb, which enable the synthesis of chiral monomers of one embodiment of the invention.

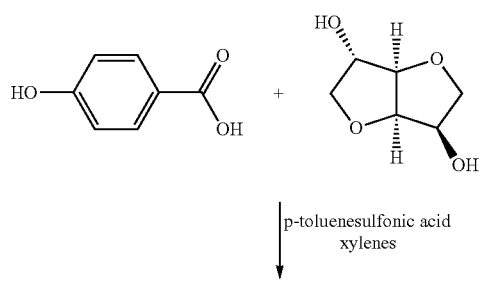

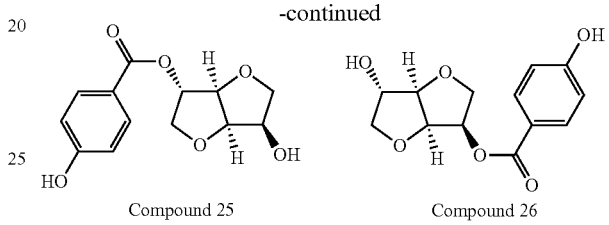

Compound 25        Compound 26

Isosorbide (10.0 g), p-hydroxybenzoic acid (9.45 g), p-toluenesulfonic acid (1.0 g), and xylenes (90 mL) were combined and heated to reflux for two hours, with azeotropic removal of water. After cooling to room temperature the xylenes were decanted away to provide a brown residue. The crude product was purified by column chromatography (2:1 ethyl acetate/hexanes). The first product to elute was the undesired 2:1 adduct, Compound 1, followed by Compound 25, followed by Compound 26.

Compound 25: $^1$H NMR (DMSO-$d_6$, 500 MHz) δ 3.39 (app t, J=8.1 Hz, 1H), 3.77 (app dd, J=8.5, 6.5 Hz, 1H), 3.94-4.01 (m, 2H), 4.16 (m, 1H), 4.51 (m, 2H), 4.90 (app d, J=6.2 Hz, 1H), 5.19 (app d, J=3.5 Hz, 1H), 6.85 (d, J=8.8 Hz, 2H), 7.80 (d, J=8.8 Hz, 2H). Compound 26: $^1$H NMR (DMSO-$d_6$, 500 MHz) δ 3.66 (app d, J=9.4 Hz, 1H), 3.72 (m, 1H), 3.78 (m, 1H), 3.87 (m, 1H), 4.11 (br s, 1H), 4.28 (app d, J=4.7 Hz, 1H), 4.78 (app t, J=5.1 Hz, 1H), 5.15 (br s, 1H), 5.24 (m, 1H), 6.86 (d, J=8.8 Hz, 2H), 7.81 (d, J=8.8 Hz, 2H).

Compound 25 is reacted with 6-bromohexanoyl chloride as described above for the synthesis of Compound 9. The resulting product is then reacted with potassium acrylate as described above for the synthesis of Compound 10. This provides a compound of formula I, wherein q+r=1. Compound 26 is similarly elaborated to provide an additional compound of formula I, wherein q+r=1.

Example 9

This example illustrates the method used to prepare a twisted nematic mixture wherein each compound was prepared separately.

Mixture 1

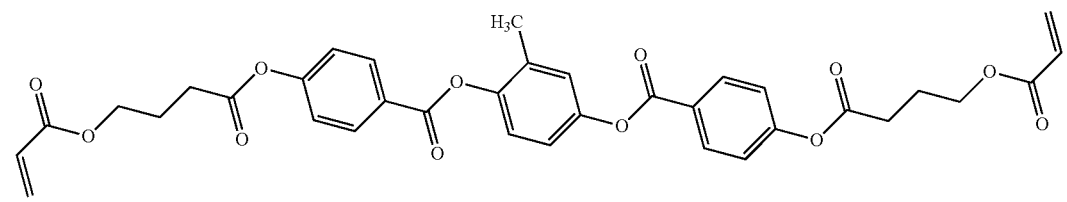

22.75 weight %

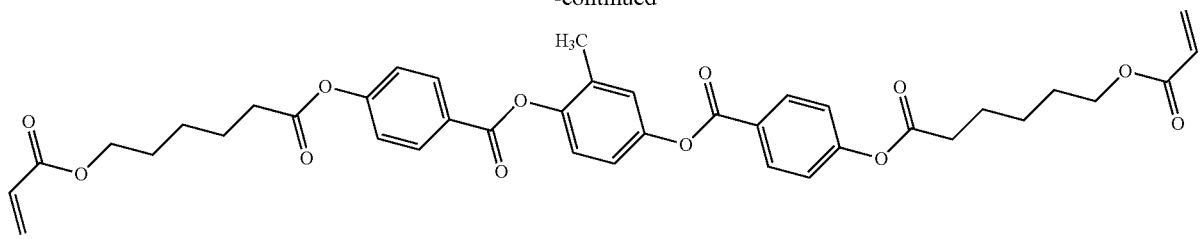

68.25 weight %

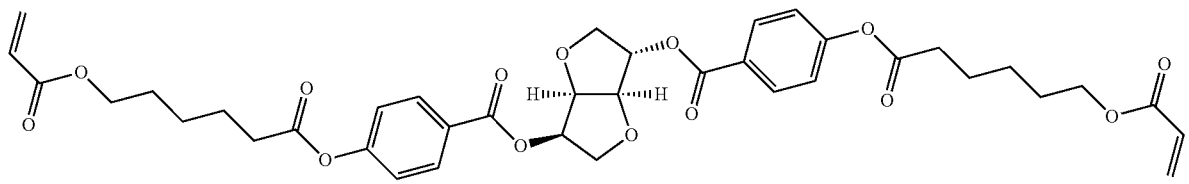

7 weight %

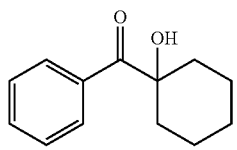

2 weight %
Irgacure(R) 184

Compound 3 (0.341 g), Compound 4 (0.114 g), Compound 10 (0.035 g) and Irgacure® 184 (0.010 g) were combined and dissolved in methylene chloride. The solution was filtered (0.45 micron filter), and solvent removed to provide Mixture 1. Phase Behavior: $1^{st}$ Heating=K 55 TN* 105 I; $1^{st}$ Cooling=I 104 TN* −53 X; $2^{nd}$ Heating=X −31 TN* 105 I. Wavelength of reflectance=532 nm.

Example 10

This example illustrates the method used to prepare a twisted nematic mixture wherein each compound was prepared separately.

Mixture 2

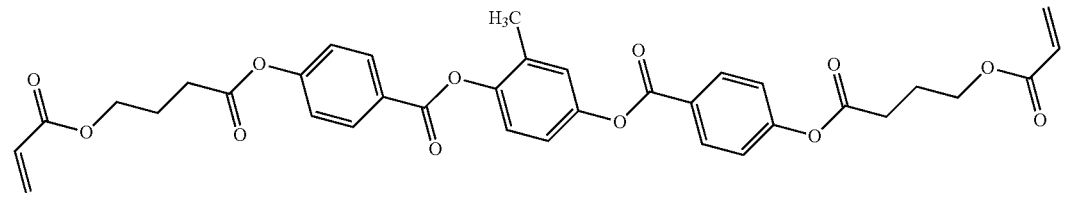

24.3 wt. %

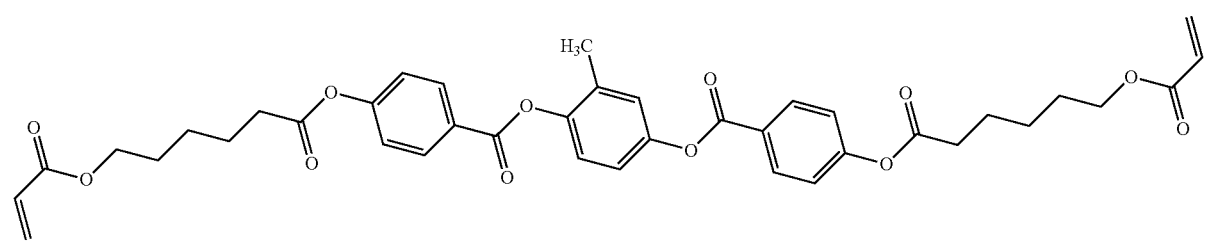

53 wt. %

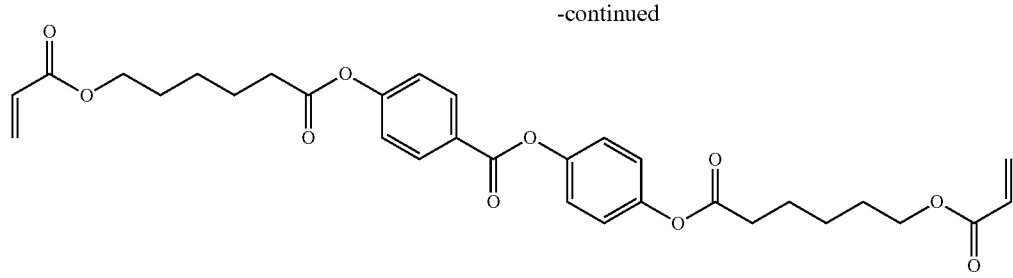

15 wt. %

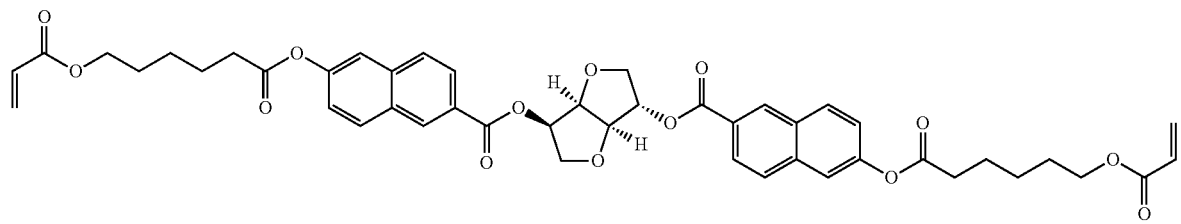

5.7 wt. %

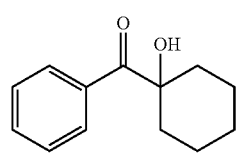

2 wt. %
Irgacure(R) 184

Mixture 2 was prepared in a similar manner as was described above for Mixture 1. Phase behavior: TN* 65 I. A polyethylene terephthalate film was hand rubbed with a Yoshikawa YA-20-R rubbing cloth. A small amount of Mixture 2 was coated by hand using a Wire Size 20 Wire Wound Lab Rod (Paul N. Gardner Company, Pompano Beach, Fla.). The wet coating was heated at 50° C. for 2 min and was exposed with a Blak-Ray Long Wave UV Mercury Lamp (UVP Inc., Upland, Calif.) for 2 min under a nitrogen atmosphere. Wavelength of Reflectance: 596 nm.

Comparative Example 1

This example demonstrates that the methodology used to prepare the conventional ether linked materials, as exemplified by formula (C-I), is not applicable to the preparation of the materials of the present invention.

The first step in the preparation of the material of formula (C-I), as disclosed in U.S. Pat. No. 5,780,629, Example 2, was followed, but replacing 2-chloroethanol with 6-bromohexanoyl chloride.

As such, 3 g ethyl 4-hydroxybenzoate, 0.036 g potassium iodide, and 2.99 g potassium carbonate were dissolved in 24 mL DMF, and 4.62 g 6-bromohexanoyl chloride was added dropwise. The reaction was heated at 90° C. for 10 hours, before being added to ice water. The product separated as an oil, in contrast to the teachings of U.S. Pat. No. 5,833,880, wherein a solid was isolated. The oily product was separated from the water using an ether extraction. The ether was dried and removed to provide 5.36 g of a yellow oil. NMR analysis indicated the presence of a complex mixture of acylation and alkylation products. The yellow oil was combined with 4.81 g potassium hydroxide and 36 mL ethanol and heated to reflux for 3 hours. The reaction was added to ice water, acidified

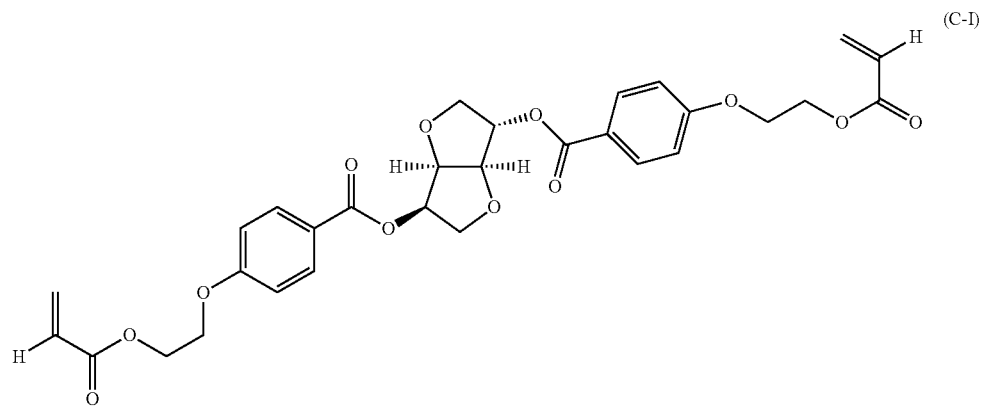

(C-I)

with concentrated HCl, filtered, washed with fresh water, and dried, to obtain 1.3 g of a white solid. NMR analysis indicated that the product was Compound 27, rather than the desired, Compound 28.

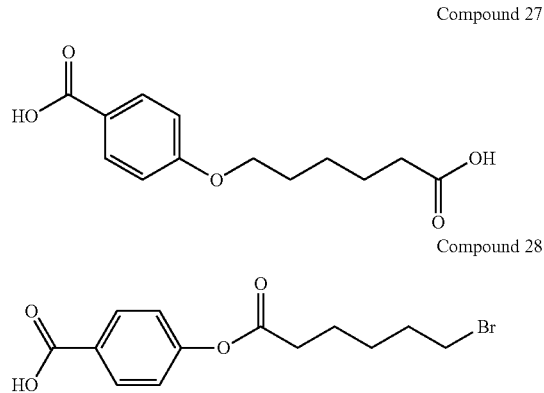

$^1$H-NMR of Compound 27: (DMSO-d$_6$, 400 MHz) δ 1.43 (m, 2H), 1.57 (m, 2H), 1.73 (m, 2H), 2.23 (t, J=7.3 Hz, 2H), 4.03 (t, J=6.5 Hz, 2H), 6.99 (d, 8.9 Hz, 2H), 7.88 (d, 8.9 Hz, 2H).

Each of the formulae shown herein describes each and all of the separate, individual compounds that can be formed in that formula by (i) selection from within the prescribed range for one of the variable, substituents or numerical coefficients while all of the other variable radicals, substituents or numerical coefficients are held constant, and (ii) performing in turn the same selection from within the prescribed range for each of the other variable radicals, substituents or numerical coefficients with the others being held constant. In addition to a selection made within the prescribed range for any of the variable radicals, substituents or numerical coefficients of only one of the members of the group described by the range, a plurality of compounds may be described by selecting more than one but less than all of the members of the group of radicals, substituents or numerical coefficients. When the selection made within the prescribed range for any of the variable radicals, substituents or numerical coefficients is a subgroup containing (a) only one of the members of the group described by the range, or (b) more than one but less than all of the members of the group, the selected member(s) are selected by omitting those member(s) of the whole group that are not selected to form the subgroup. The compound, or plurality of compounds, may in such event be described as containing one or more variable radicals, substituents or numerical coefficients each of which variable radicals, substituents or numerical coefficients is defined by the members of the whole group, described by the range for that variable radical, substituent or numerical coefficient in the absence of the member(s) omitted to form the subgroup.

Certain features of this invention are described herein in the context of an embodiment that combines various such features together, whether as described in the disclosure or in one of the drawings. The scope of the invention is not, however, limited by the description of only certain features within any particular embodiment, and the invention also includes (1) a subcombination of fewer than all of the features of any described embodiment, which subcombination is characterized by the absence of the features omitted to form the subcombination; (2) each of the features, individually, included within the combination of the described embodiment; and (3) other combinations of features formed from one or more or all of the features of the described embodiment together with other features as disclosed elsewhere herein.

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of this invention is stated or described as comprising, including, containing, having, being composed of or being constituted by or of certain features or elements, one or more features or elements in addition to those explicitly stated or described may be present in the embodiment. An alternative embodiment of this invention, however, may be stated or described as consisting essentially of certain features or elements, in which embodiment features or elements that would materially alter the principle of operation or the distinguishing characteristics of the embodiment are not present therein. A further alternative embodiment of this invention may be stated or described as consisting of certain features or elements, in which embodiment, or in insubstantial variations thereof, only the features or elements specifically stated or described are present.

In this specification, unless explicitly stated otherwise or indicated to the contrary by the context of usage, (a) amounts, sizes, formulations, parameters, and other quantities and characteristics recited herein, particularly when modified by the term "about", may but need not be exact, and may be approximate and/or larger or smaller than stated (as desired), reflecting tolerances, conversion factors, rounding off, measurement error and the like, as well as the inclusion within a stated value of those values outside it that have, within the context of this invention, functional and/or operable equivalence to the stated value;

(b) all numerical quantities of parts, percentage or ratio are given as parts, percentage or ratio by weight;

(c) use of the indefinite article "a" or "an" with respect to a statement or description of the presence of an element or feature of this invention, does not limit the presence of the element or feature to one in number;

(d) the words "include", "includes" and "including" are to be read and interpreted as if they were followed by the phrase "without limitation" if in fact that is not the case; and (e) the word "or", as used herein, is inclusive; more specifically, the phrase "A or B" means "A, B, or both A and B"; and use of "or" in an exclusive sense is designated, for example, by terms such as "either A or B" and "one of A or B".

What is claimed is:

1. A process comprising
a) providing a chiral organic diol;
b) reacting the chiral organic diol with one or more functionalized alkyl acids or acid halide(s) of the Formula (II):

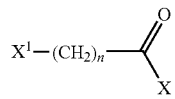

(II)

wherein X is Cl, Br or OH; $X^1$ is selected from the group: Cl, Br, I, —OMs, —OTs, and —OTf; and n is an integer equal to 3 to 20; in a first reaction solvent at a first reaction temperature to provide one or more polyfunctionalized ester(s) and a first spent reaction mixture; and
c) reacting the one or more polyfunctionalized ester(s) with a (meth)acrylate salt in the presence of a phase transfer catalyst, and a second reaction solvent at a second reaction temperature; to provide one or more poly (meth)acrylate ester(s) and a second spent reaction mixture;
wherein
step (b) further comprises addition of an amine base in an amount of about 0.8 to about 5 equivalents per equivalent of the functionalized alkyl acid or alkyl acid halide(s); and
step (c) further comprises addition of one or more radical inhibitors.

2. A process comprising
a) providing a chiral organic diol;
b) reacting the chiral organic diol with one or more functionalized alkyl acids or acid halide(s) of the Formula (II):

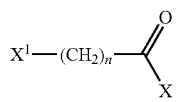

(II)

wherein X is Cl, Br or OH; $X^1$ is selected from the group: Cl, Br, I, —OMs, —OTs, and —OTf; and n is an integer equal to 3 to 20; in a first reaction solvent at a first reaction temperature to provide one or more polyfunctionalized ester(s) and a first spent reaction mixture; and
c) reacting the one or more polyfunctionalized ester(s) with a (meth)acrylate salt in the presence of a phase transfer catalyst, and a second reaction solvent at a second reaction temperature; to provide one or more poly (meth)acrylate ester(s) and a second spent reaction mixture; wherein the second reaction solvent is an aprotic solvent having a dipole moment of less than about 3.5; and the (meth)acrylate salt is selected from an alkali metal salt or ammonium salt.

3. A process comprising
a) providing a chiral organic diol;
b) reacting the chiral organic diol with one or more functionalized alkyl acids or acid halide(s) of the Formula (II):

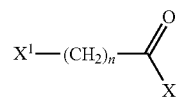

(II)

wherein X is Cl, Br or OH; $X^1$ is selected from the group: Cl, Br, I, —OMs, —OTs, and —OTf; and n is an integer equal to 3 to 20; in a first reaction solvent at a first reaction temperature to provide one or more polyfunctionalized ester(s) and a first spent reaction mixture;
c) separating the one or more polyfunctionalized ester(s) from the first spent reaction mixture;
d) reacting the one or more polyfunctionalized ester(s) with a (meth)acrylate salt in the presence of a phase transfer catalyst, and a second reaction solvent at a second reaction temperature; to provide one or more poly (meth)acrylate ester(s) and a second spent reaction mixture; and
e) separating the one or more poly (meth)acrylate ester(s) from the second spent reaction mixture.

4. A process comprising
a) providing a chiral organic diol;
b) reacting the chiral organic diol with one or more functionalized alkyl acids or acid halide(s) of the Formula (II):

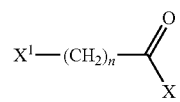

(II)

wherein X is Cl, Br or OH; $X^1$ is selected from the group: Cl, Br, I, —OMs, —OTs, and —OTf; and n is an integer equal to 3 to 20; in a first reaction solvent at a first reaction temperature to provide one or more polyfunctionalized ester(s) and a first spent reaction mixture; and
c) reacting the one or more polyfunctionalized ester(s) with a (meth)acrylate salt in the presence of a phase transfer catalyst, and a second reaction solvent, wherein the second reaction solvent comprises the first spent reaction mixture, at a second reaction temperature; to provide one or more poly (meth)acrylate ester(s) and a second spent reaction mixture.

5. A process comprising
a) providing a chiral organic diol;
b) reacting the chiral organic diol with two or more functionalized alkyl acids or alkyl acid halides of the Formula (II):

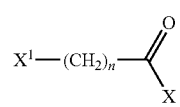

(II)

wherein X is Cl, Br or OH; $X^1$ is selected from the group: Cl, Br, I, —OMs, —OTs, and —OTf; and n is an integer equal to 3 to 20; in a first reaction solvent at a first reaction temperature to provide a mixture of at least three polyfunctionalized esters and a first spent reaction mixture; and c) reacting the mixture of polyfunctionalized esters with a (meth)acrylate salt in the presence of a phase transfer catalyst, and a second reaction solvent at a second reaction temperature; to provide poly (meth)acrylate esters and a second spent reaction mixture.

6. A process for preparing a chiral bisacrylate comprising contacting 6-hydroxyhexanoic acid with acryloyl chloride to prepare 6-acryloyloxyhexanoic acid; contacting 6-acryloyloxyhexanoic acid with oxalyl chloride to prepare the acid chloride of 6-acryloyloxyhexanoic acid; contacting the acid chloride of 6-acryloyloxyhexanoic acid with 4'-hydroxy-4-biphenylcarboxylic acid to prepare the following compound:

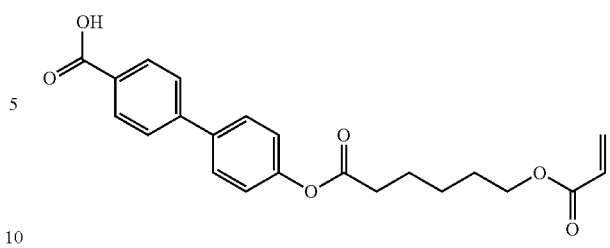

contacting the above compound with oxalyl chloride to prepare the acid chloride thereof; contacting the acid chloride of the above compound with isosorbide to prepare the following compound:

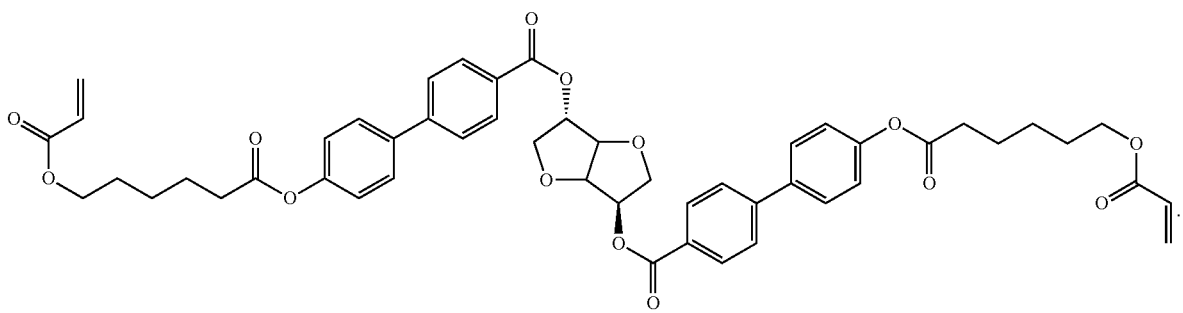

* * * * *